(12) United States Patent
Montgomery et al.

(10) Patent No.: US 12,702,539 B2
(45) Date of Patent: Aug. 11, 2026

(54) EMBOLIC FILTER WITH FLEXIBLE COUPLING

(71) Applicant: W. L. Gore & Associates, Inc., Newark, DE (US)

(72) Inventors: William D. Montgomery, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 192 days.

(21) Appl. No.: 17/285,023

(22) PCT Filed: Oct. 17, 2019

(86) PCT No.: PCT/US2019/056737

§ 371 (c)(1),
(2) Date: Apr. 13, 2021

(87) PCT Pub. No.: WO2020/081814

PCT Pub. Date: Apr. 23, 2020

(65) Prior Publication Data

US 2022/0000600 A1 Jan. 6, 2022

Related U.S. Application Data

(60) Provisional application No. 62/747,026, filed on Oct. 17, 2018.

(51) Int. Cl.
*A61F 2/01* (2006.01)
*A61B 17/00* (2006.01)

(52) U.S. Cl.
CPC ........... *A61F 2/0105* (2020.05); *A61F 2/011* (2020.05); *A61B 2017/00778* (2013.01);
(Continued)

(58) Field of Classification Search
CPC ........ A61F 2/0105; A61F 2/011; A61F 2/013; A61F 2002/016; A61F 2002/018;
(Continued)

(56) References Cited

U.S. PATENT DOCUMENTS

| 1,594,419 A | 8/1926 | Kruse |
|---|---|---|
| 5,104,404 A | 4/1992 | Wolff |

(Continued)

FOREIGN PATENT DOCUMENTS

| CN | 110680459 A | 1/2020 |
|---|---|---|
| EP | 1310219 A2 | 5/2003 |

(Continued)

OTHER PUBLICATIONS

Annex to Form PCT/ISA/206 Communication Relating to the Results of the Partial International Search for PCT/US2012/059769 mailed Dec. 19, 2012 corresponding to U.S. Appl. No. 13/448,277.

(Continued)

*Primary Examiner* — Kathleen S Holwerda
*Assistant Examiner* — James R McGinnity

(57) ABSTRACT

Described embodiments are directed toward an embolic filter system. The embolic filter system generally includes a filter and an elongated element that can be articulated relative to one another. In some examples, the filter includes an articulation element that facilitates articulation between a proximal and distal end of the filter. In some examples, an articulation element is positioned between the filter and the elongate element.

42 Claims, 15 Drawing Sheets

(52) U.S. Cl.
CPC ......... *A61F 2/013* (2013.01); *A61F 2002/016* (2013.01); *A61F 2002/018* (2013.01); *A61F 2210/0014* (2013.01); *A61F 2230/0067* (2013.01); *A61F 2230/0091* (2013.01)

(58) Field of Classification Search
CPC ...... A61F 2210/0014; A61F 2230/0067; A61F 2230/0091; A61F 2/01; A61F 2/86; A61F 2/88; A61F 2/91; A61F 2230/0069; A61B 2017/00778; A61B 2017/00867
See application file for complete search history.

(56) References Cited

U.S. PATENT DOCUMENTS 5,152,777 A 10/1992 Goldberg et al.
5,569,184 A 10/1996 Crocker et al.
5,649,906 A 7/1997 Gory et al.
5,776,161 A 7/1998 Globerman
5,876,449 A 3/1999 Starck et al.
6,042,606 A 3/2000 Frantzen
6,179,859 B1 1/2001 Bates et al.
6,273,900 B1 8/2001 Nott et al.
6,361,545 B1 3/2002 Macoviak et al.
6,440,120 B1 8/2002 Maahs
6,468,291 B2 10/2002 Bates et al.
6,676,683 B1 1/2004 Addis
6,942,681 B2 9/2005 Johnson
7,083,633 B2 8/2006 Morrill et al.
7,344,515 B2 3/2008 Coyle
7,585,309 B2 9/2009 Larson
7,648,495 B2 1/2010 Bates
7,771,452 B2 8/2010 Pal et al.
7,803,168 B2 9/2010 Gifford et al.
7,837,702 B2 11/2010 Bates
7,842,063 B2 11/2010 Gilson et al.
7,972,361 B2 7/2011 Corcoran et al.
8,257,384 B2 9/2012 Bates
8,545,552 B2 10/2013 Garrison et al.
8,702,744 B2 4/2014 Bates
8,728,113 B2 5/2014 Bates
8,753,370 B2 6/2014 Lashinski
8,876,796 B2 11/2014 Fifer et al.
9,089,406 B2 7/2015 Basu et al.
9,186,238 B2 11/2015 Eidenschink et al.
9,220,615 B2 12/2015 Denison et al.
9,314,605 B2 4/2016 Arcaro et al.
9,498,225 B2 11/2016 Zhadkevich
9,526,864 B2 12/2016 Quick
9,526,865 B2 12/2016 Quick
9,561,347 B2 2/2017 Holm et al.
9,839,540 B2 12/2017 Armstrong et al.
9,855,157 B2 1/2018 Cattaneo et al.
9,913,740 B2 3/2018 Perko
9,943,397 B2 4/2018 Bonnette et al.
10,143,545 B2 12/2018 Friedman
11,298,218 B2 4/2022 Montgomery et al.
2002/0004667 A1 1/2002 Adams et al.
2002/0138094 A1 9/2002 Borillo et al.
2002/0161394 A1 10/2002 Macoviak et al.
2002/0169474 A1 11/2002 Kusleika et al.
2003/0004536 A1 1/2003 Boylan et al.
2003/0045897 A1 3/2003 Huter et al.
2003/0065354 A1 4/2003 Boyle et al.
2003/0144686 A1 7/2003 Martinez et al.
2003/0150821 A1 8/2003 Bates et al.
2004/0006366 A1 1/2004 Huter et al.
2004/0006367 A1 1/2004 Johnson et al.
2004/0064099 A1 4/2004 Chiu
2004/0098026 A1 5/2004 Joergensen et al.
2004/0102834 A1 5/2004 Nakano et al.
2004/0167437 A1 8/2004 Sharrow et al.
2004/0172055 A1 9/2004 Huter et al.
2005/0038470 A1* 2/2005 van der Burg ... A61B 17/12172 606/213
2005/0043756 A1 2/2005 Lavelle et al.
2005/0096691 A1 5/2005 Groothuis et al.
2005/0187570 A1 8/2005 Nguyen et al.
2005/0288769 A1 12/2005 Globerman
2006/0004329 A1 1/2006 Hebert et al.
2006/0057183 A1 3/2006 Nakano et al.
2006/0058837 A1 3/2006 Bose et al.
2006/0125144 A1 6/2006 Weber et al.
2006/0129229 A1 6/2006 Fukaya et al.
2006/0173490 A1 8/2006 Lafontaine et al.
2007/0038289 A1 2/2007 Nishide et al.
2007/0100279 A1 5/2007 Bates
2007/0233183 A1 10/2007 Brady et al.
2007/0244503 A1 10/2007 Casey et al.
2008/0004690 A1 1/2008 Robaina
2008/0167678 A1 7/2008 Morsi
2008/0167679 A1* 7/2008 Papp ...................... A61F 2/013 29/34 R
2008/0249633 A1 10/2008 Wu
2009/0036970 A1 2/2009 Ma et al.
2009/0326575 A1 12/2009 Galdonik et al.
2010/0076482 A1 3/2010 Shu et al.
2010/0106182 A1 4/2010 Patel et al.
2010/0168785 A1 7/2010 Parker
2010/0234938 A1 9/2010 Taheri et al.
2010/0268264 A1 10/2010 Bonnette et al.
2010/0305604 A1 12/2010 Pah
2011/0098738 A1 4/2011 Hunt
2011/0137399 A1 6/2011 Chomas et al.
2011/0160742 A1 6/2011 Ferrera et al.
2011/0307002 A1* 12/2011 Gilson ................. A61F 2/0095 606/200
2012/0035650 A1* 2/2012 Linder ..................... A61F 2/01 606/200
2012/0209311 A1 8/2012 Grandfield et al.
2012/0253313 A1 10/2012 Galdonik et al.
2013/0096606 A1* 4/2013 Bruchman ........... A61B 17/221 606/200
2013/0123705 A1 5/2013 Holm et al.
2013/0123905 A1 5/2013 Abunassar et al.
2013/0144328 A1 6/2013 Weber et al.
2013/0178891 A1 7/2013 Russell et al.
2013/0184742 A1 7/2013 Ganesan et al.
2013/0253570 A1 9/2013 Bates
2013/0253571 A1 9/2013 Bates
2013/0338761 A1 12/2013 Plowiecki et al.
2014/0018912 A1 1/2014 Delaloye et al.
2014/0031857 A1 1/2014 Richardson
2014/0135736 A1 5/2014 Hebert
2014/0236221 A1 8/2014 Zhadkevich
2014/0303667 A1 10/2014 Cox et al.
2015/0066075 A1 3/2015 Russell et al.
2015/0066131 A1* 3/2015 Luong ..................... A61F 2/962 623/1.11
2015/0182361 A1 7/2015 Ferrera et al.
2015/0223920 A1 8/2015 Bruchman et al.
2016/0022292 A1 1/2016 Stigall et al.
2016/0120636 A1 5/2016 Gera et al.
2016/0143721 A1* 5/2016 Rosenbluth .... A61B 17/320725 600/200
2016/0166372 A1* 6/2016 Villareal .................. A61F 2/01 156/149
2016/0199169 A1 7/2016 Tafti et al.
2016/0302924 A1* 10/2016 Boutillette ............ A61M 25/09
2017/0000493 A1 1/2017 Boehm et al.
2017/0202657 A1* 7/2017 Lee .......................... A61F 2/01
2017/0259042 A1 9/2017 Nguyen et al.
2018/0087975 A1* 3/2018 Ellis ...................... G01K 11/20
2018/0125683 A1 5/2018 Kariniemi et al.
2018/0147041 A1* 5/2018 Chouinard .............. A61F 2/013
2018/0235743 A1 8/2018 Farago et al.
2019/0000615 A1 1/2019 Tayeb et al.
2019/0015120 A1 1/2019 Molaei
2019/0231566 A1* 8/2019 Tassoni ............ A61B 17/12022
2019/0374328 A1 12/2019 Montgomery et al.
2019/0388108 A1 12/2019 Ferrera et al.
2020/0253709 A1 8/2020 Russell et al.
2020/0406018 A1* 12/2020 Malek .................. A61M 25/04

(56) References Cited

U.S. PATENT DOCUMENTS

| | | | |
|---|---|---|---|
| 2021/0236257 A1* | 8/2021 | Walzman ......... | A61B 17/32037 |
| 2022/0296354 A1 | 9/2022 | Montgomery et al. | |
| 2024/0299151 A1 | 9/2024 | Montgomery | |

FOREIGN PATENT DOCUMENTS

| | | | |
|---|---|---|---|
| EP | 1594419 | A1 | 11/2005 |
| EP | 2967602 | A1 | 1/2016 |
| JP | 05-130996 | A | 5/1993 |
| JP | 2002-537943 | A | 11/2002 |
| JP | 2003-220062 | A | 8/2003 |
| JP | 2004-532667 | A | 10/2004 |
| JP | 2008-512181 | A | 4/2008 |
| JP | 2011-525405 | A | 9/2011 |
| JP | 2011-234769 | A | 11/2011 |
| JP | 201234769 | * | 11/2011 |
| JP | 2012-509113 | A | 4/2012 |
| JP | 2012-510352 | A | 5/2012 |
| JP | 2013-005859 | A | 1/2013 |
| JP | 2013-512735 | A | 4/2013 |
| JP | 2014-511223 | A | 5/2014 |
| JP | 2014-534006 | A | 12/2014 |
| JP | 2016-093542 | A | 5/2016 |
| KR | 10-2011-0095895 | A | 8/2011 |
| WO | 96/26689 | A1 | 9/1996 |
| WO | 99/16382 | A2 | 4/1999 |
| WO | 99/32050 | A1 | 7/1999 |
| WO | 00/53120 | A1 | 9/2000 |
| WO | 02/43595 | A2 | 6/2002 |
| WO | 2004/026175 | A1 | 4/2004 |
| WO | 2005/072645 | A1 | 8/2005 |
| WO | 2006/031410 | A2 | 3/2006 |
| WO | 2009/055782 | A1 | 4/2009 |
| WO | 2009/068596 | A1 | 6/2009 |
| WO | 2010/008451 | A2 | 1/2010 |
| WO | 2010/026240 | A1 | 3/2010 |
| WO | 2010/059737 | A2 | 5/2010 |
| WO | 2013/126618 | A1 | 8/2013 |
| WO | 2014/079291 | A1 | 5/2014 |
| WO | 2014/145469 | A1 | 9/2014 |
| WO | 2014/145892 | A2 | 9/2014 |
| WO | 2015/085307 | A1 | 6/2015 |
| WO | 2018/183321 | A1 | 10/2018 |
| WO | 2020/081814 | A1 | 4/2020 |

OTHER PUBLICATIONS

International Preliminary Report on Patentability received for PCT Patent Application No. PCT/US2012/059769, mailed on May 1, 2014, 10 pages.

International Preliminary Report on Patentability received for PCT Patent Application No. PCT/US2018/014395, mailed on Aug. 1, 2019 , 11 pages.

International Preliminary Report on Patentability received for PCT Patent Application No. PCT/US2019/056737, mailed on Apr. 29, 2021, 7 pages.

International Search Report and Written Opinion for PCT/US2012/059769 mailed Apr. 19, 2013, correspondin to U.S. Appl. No. 13/448,277.

International Search Report and Written Opinion received for PCT Patent Application No. PCT/US2018/014395, mailed on Aug. 8, 2018, 14 pages.

International Search Report and Written Opinion received for PCT Patent Application No. PCT/US2019/056737, mailed on Jan. 14, 2020, 13 pages.

International Preliminary Report on Patentability received for PCT Patent Application No. PCT/JP2018/045283, mailed on Aug. 13, 2020, 15 pages (9 pages of English Translation and 6 pages of Original Document).

International Search Report and Written Opinion received for PCT Patent Application No. PCT/JP2018/045283, mailed on Feb. 26, 2019, 17 pages (9 pages of English Translation and 8 pages of Original Document).

International Search Report and Written Opinion received for PCT Patent Application No. PCT/US2022/012571, mailed on Apr. 29, 2022, 11 pages.

European Search Report for EP Patent Application No. 24194402.4, Issued on Nov. 13, 2024, 15 pages.

International Preliminary Report on Patentability received for PCT Patent Application No. PCT/US2022/012571, mailed on Jul. 27, 2023, 8 pages.

* cited by examiner 1000
5000

EMBOLIC FILTER WITH FLEXIBLE COUPLING

CROSS-REFERENCE TO RELATED APPLICATION

This application is a national phase application of PCT Application No. PCT/US2019/056737, internationally filed on Oct. 17, 2019, which claims the benefit of U.S. Provisional Application No. 62/747,026, filed Oct. 17, 2018, both of which are incorporated herein by reference in their entireties for all purposes.

BACKGROUND

Endovascular procedures address a broad array of medical needs, including endovascular access, diagnosis, and/or repair through minimally invasive or relatively less invasive means than surgical approaches. During some endovascular procedures, embolic debris may become dislodged or circulated in the vasculature. Circulation of embolic debris can cause mild to extreme cardiovascular complications, leading to stroke and even death.

Embolic protection devices have been developed and used in connection with such endovascular procedures to help mitigate the risks associated with various endovascular procedures. Some embolic protection devices operate to capture embolic debris and filter the same from the blood. The captured embolic debris can be aspirated (e.g., actively or passively) prior to removal of the embolic protection device. Additionally or alternatively, the embolic protection device can be configured to trap the embolic debris within the embolic protection device such that the embolic debris is retained by the embolic protection device upon its removal from the vasculature. However, a common risk of these procedures is the unintentional release of some or all of the captured embolic debris back into the vasculature during the removal process.

Proper orientation of the embolic protection devices within the vasculature is an important factor in the facilitation of embolic debris capture and removal. However, while conventional devices may be deployable within tortuous vasculature, some lack the means for orienting or repositioning the device within the vasculature after it has been deployed. Poor orientation of embolic protection devices may result in embolic debris bypassing the embolic protection device, such as by way of one or more gaps between the embolic protection device and a vessel wall and/or by embolic debris not being fully captured by the embolic protection device resulting in unintended ejection of the embolic debris back into the blood upon removal of the embolic protection device from the vasculature. Proper orientation is especially difficult in tortuous anatomy.

SUMMARY

According to a first example ("Example 1") a medical device includes, an elongate element having a first end and a second end, and an embolic filter assembly including a frame having an attachment section, a capture section distal to the attachment section, and an intermediate section between the attachment section and the capture section, the attachment section of the embolic filter assembly being coupled to the elongate element at one of the first and second ends, wherein the intermediate section is adapted to allow for relative articulation between the capture section of the frame and the attachment section of the frame, and wherein the attachment section, the capture section, and the intermediate section are formed of the same material.

According to another example ("Example 2") further to Example 1, the capture section is radially expandable relative to the attachment section such that the embolic filter assembly is configured to transition between a compressed state and an expanded state in situ.

According to another example ("Example 3") further to any of the Examples, the capture section is radially expandable relative to the intermediate section.

According to another example ("Example 4") further to any of the Examples, the frame is configured such that the capture section is self-expandable.

According to another example ("Example 5") further to any of the Examples, the frame includes a metallic alloy.

According to another example ("Example 6") further to Example 5, the metallic alloy includes nitinol.

According to another example ("Example 7") further to any of the Examples, the frame is a unibody such that the attachment section, the capture section, and the intermediate section define a single monolithic component.

According to another example ("Example 8") further to any of the Examples, the intermediate section is helically shaped.

According to another example ("Example 9") further to any of the Examples, the frame is formed of a cut tube having a body and a lumen extending therethrough.

According to another example ("Example 10") further Example 9, the cut tube is a laser cut tube.

According to another example ("Example 11") further to any of Examples 9 to 10, wherein the intermediate section is defined by a helical cut through the body of the tube that exposes the lumen of the tube.

According to another example ("Example 12") further to any of Examples 1 to 8, wherein the attachment section, the capture section, and the intermediate section are affixed to one another.

According to another example ("Example 13") further to Example 12, wherein one or more of the capture section and the intermediate section include a wire frame.

According to another example ("Example 14") further to Example 13, wherein the intermediate section includes a helically wound wire.

According to another example ("Example 15") further to any of the Examples, the intermediate section is adapted to bend.

According to another example ("Example 16") further to any of the Examples, the attachment section of the frame defines a first longitudinal axis, and wherein the capture section defines a second longitudinal axis, and wherein the intermediate section is adapted to bend such that the first longitudinal axis can be deflected up to 270 degrees relative to the second longitudinal axis.

According to another example ("Example 17") further to any of Examples 1-15, wherein the attachment section of the frame defines a first longitudinal axis, and wherein the capture section defines a second longitudinal axis, and wherein the intermediate section is adapted to bend such that the first longitudinal axis can be deflected up to 180 degrees relative to the second longitudinal axis.

According to another example ("Example 18") further to any of Examples 1-15, wherein the attachment section of the frame defines a first longitudinal axis, and wherein the capture section defines a second longitudinal axis, and wherein the intermediate section is adapted to bend such that the first longitudinal axis can be deflected up to 90 degrees relative to the second longitudinal axis.

According to another example ("Example 19") further to any of the Examples, the frame has a first end and a second end and a lumen extending through the frame from the first end to the second end.

According to another example ("Example 20") further to any of the Examples, the embolic filter assembly further includes a filter material disposed along the frame.

According to another example ("Example 21") further to Example 20, the filter material is disposed along the intermediate section of the frame.

According to another example ("Example 22") further to any of Examples 20 to 21, the filter material is impermeable to embolic debris greater than about 140 μm.

According to another example ("Example 23") further to any of Examples 20 to 22, the filter material is configured to constrain elongation of the intermediate section to less than a yield point of the intermediate section.

According to another example ("Example 24") further to any of Examples 20 to 23, the filter material is configured to stretch to accommodate one or more of bending and elongation of the intermediate portion of the frame, wherein a yield strength of the filter material exceeds a yield strength of the intermediate portion.

According to another example ("Example 25") further to any of Examples 20 to 24, the filter material includes a polymeric material.

According to another example ("Example 26") further to Example 25, wherein the polymeric material includes ePTFE.

According to another example ("Example 27") further to any of the Examples, one or more of the capture section, the attachment section, and the elongate element are operable to articulate about the intermediate section.

According to another example ("Example 28") a system includes an elongate element, a medical device including an expandable portion, and a union situated between the expandable portion of the medical device and the elongate element, the union defining a coupling between the elongate element and the medical device such that the expandable portion of the medical device extends distal to a distal end of the elongate element, the coupling being adapted to allow for relative articulation between the medical device and the elongate element, wherein the medical device and the union include the same material.

According to another example ("Example 29") further to Example 28, the medical device is an embolic filter.

According to another example ("Example 30") further to any of Examples 28 to 29, the union includes a helically shaped portion that is adapted to bend.

According to another example ("Example 31") further to any of Examples 28 to 30, the union includes a lumen that is adapted to allow embolic debris to pass therethrough from the medical device to the elongate element, and wherein the union is covered by a filter material.

According to another example ("Example 32") further to Example 31, the filter material is impermeable to embolic debris greater than about 140 μm.

According to another example ("Example 33") further to any of Examples 31 to 32, the filter material is configured to constrain elongation of the intermediate section to less than a yield point of the intermediate section.

According to another example ("Example 34") further to any of Examples 31 to 33, the filter material is configured to stretch to accommodate one or more of bending and elongation of the intermediate portion of the frame, wherein a yield strength of the filter material exceeds a yield strength of the intermediate portion.

According to another example ("Example 35") further to any of Examples 31 to 34, the filter material includes a polymeric material.

According to another example ("Example 36") further to Example 35, the polymeric material includes ePTFE.

According to another example ("Example 37") further to any of Examples 28 to 36, the union is configured such that the elongate element can be articulated up to 45 degrees relative to the medical device.

According to another example ("Example 38") further to any of Examples 28 to 36, the union is configured such that the elongate element can be articulated up to 60 degrees relative to the medical device.

According to another example ("Example 39") further to any of Examples 28 to 36, the union is configured such that the elongate element can be articulated up to 90 degrees relative to the medical device.

According to another example ("Example 40") further to any of the Examples 28 to 36, the union is configured such that the elongate element can be articulated up to 180 degrees relative to the medical device.

According to another example ("Example 41") further to any of Examples 28 to 36, the union is configured such that the elongate element can be articulated up to 270 degrees relative to the medical device.

According to another example ("Example 42") further to any of the Examples, embolic debris captured by the embolic filter assembly can be aspirated through a lumen of the elongate element.

According to another example ("Example 43") further to any of the Examples, the elongate element is configured to be cut to a desired length prior to use.

According to another example ("Example 44") a medical system includes a first elongate element having a first end, a second end, and a first length, the elongate element being configured such that the first length can be reduced to a second shorter length, an embolic filter coupled to the first end of the first elongate element, the embolic filter being configured such that it is transitionable between a radially collapsed configuration and a radially expanded configuration in situ, the embolic filter being self-expandable, wherein the first elongate element is receivable within a second elongate element, such that the first elongate element is advanceable and retractable within the second elongate element, and wherein the second elongate element is configured to be advance within a patient.

According to another example ("Example 45") a method of assembling a medical device includes providing an embolic filter assembly including a filter component coupled to a distal end of a first elongate element, providing a second elongate element having a lumen extending therethrough, inserting a proximal end of the first elongate element into the lumen of the second elongate element, and proximally advancing the proximal end of the first elongate element through the lumen of the second elongate element until the proximal end of the first elongate element is withdrawn from the proximal end of the second elongate element and until the filter component is received within the lumen of the second elongate element such that the first elongate element is advanceable and retractable within the second elongate element, and wherein the second elongate element is configured to be advance within a patient.

According to another example ("Example 46") a method of assembling a medical device includes providing an embolic filter assembly including a filter component coupled to a distal end of a first elongate element, providing a constraining sheath having a first end, a second end, and a lumen extending therethrough, providing a second elongate element having a lumen extending therethrough, inserting a proximal end of the first elongate element into the lumen of the constraining sheath at the first end of the constraining sheath, advancing the proximal end of the first elongate element through the lumen of the constraining sheath until the proximal end of the first elongate element is withdrawn from the second end of the constraining sheath and until the filter component is received within the lumen of the constraining sheath, inserting the first end of the constraining sheath into the lumen of the second elongate element at a proximal end of the second elongate element, and advancing the first elongate element and the filter component distally relative to the constraining sheath and the second elongate element until the filter component is received within the lumen of the second elongate element.

According to another example ("Example 47") further to Example 46, the constraining sheath is configured to split, and the method further includes splitting the constraining sheath and removing the constraining sheath from the first and second elongate elements.

According to another example ("Example 48") further to any of Examples 46 to 47, the second elongate element is configured to be inserted into a patient.

According to another example ("Example 49") further to Example 48, the filter component is deployable from the distal end of the second elongate element when the second elongate element is inserted into the patient.

According to another example ("Example 50") a method of treatment includes providing an embolic filter assembly including a filter component coupled to a distal end of a first elongate element, providing a constraining sheath having a first end, a second end, and a lumen extending therethrough, providing a second elongate element having a lumen extending therethrough, inserting a proximal end of the first elongate element into the lumen of the constraining sheath at the first end of the constraining sheath, advancing the proximal end of the first elongate element through the lumen of the constraining sheath until the proximal end of the first elongate element is withdrawn from the second end of the constraining sheath and until the filter component is received within the lumen of the constraining sheath, inserting the first end of the constraining sheath into the lumen of the second elongate element at a proximal end of the second elongate element, and advancing the first elongate element and the filter component distally relative to the constraining sheath and the second elongate element until the filter component is received within the lumen of the second elongate element, advancing the second elongate element to a treatment area within a patient, and deploying the filter component from the distal end of the second elongate element.

According to another example ("Example 51") further to Example 50, the second elongate element is advanced to the treatment area within the patient prior to inserting the first end of the constraining sheath into the lumen of the second elongate element at a proximal end of the second elongate element.

According to another example ("Example 52") further to any of Examples 50 to 51, the constraining sheath is configured to split, the method further including splitting the constraining sheath and removing the constraining sheath from the first and second elongate elements.

According to another example ("Example 53") further to any of Examples 45 to 52, the first elongate element has a first length, and wherein the first elongate element is configured such that the first length can be altered to a second shorter length after the first elongate element is received within the lumen of the second elongate element.

According to another example ("Example 54") further to Example 53, the first elongate element is configured such that the elongate element can be cut to alter the first length to the second shorter length.

According to another example ("Example 55") further to any of Examples 53 to 54, wherein the first elongate element includes a plurality of predetermined removable sections such that the elongate element can altered from the first length to the second shorter length.

According to another example ("Example 56") further to any of Examples 45 to 55, the embolic filter assembly includes a lumen extending therethrough from the filter component to the proximal end of the first elongate element, the method further includes coupling a hub to the proximal end of the first elongate element to fluidly seal the lumen of the embolic filter assembly.

According to another example ("Example 57") further to any of Examples 45 to 56, wherein the second elongate element is a commercial over the shelf catheter.

According to another example ("Example 58") further to any of Examples 45 to 57, the first elongate element is color-coded to indicate a diameter of the first elongate element, wherein a first color indicates a first diameter and wherein a second color indicates a second different diameter.

According to another example ("Example 59") further to any of Examples 45 to 58, the filter component is coupled to the first elongate element via a flexible coupling such that the filter component and the first elongate element are operable to angulate relative to one another.

According to another example ("Example 59") further to any of Examples 45 to 59, the treatment area is within a vasculature of the patient.

While multiple examples are disclosed, still other examples will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate examples, and together with the description serve to explain the principles of the disclosure.

DETAILED DESCRIPTION

Figure 1:
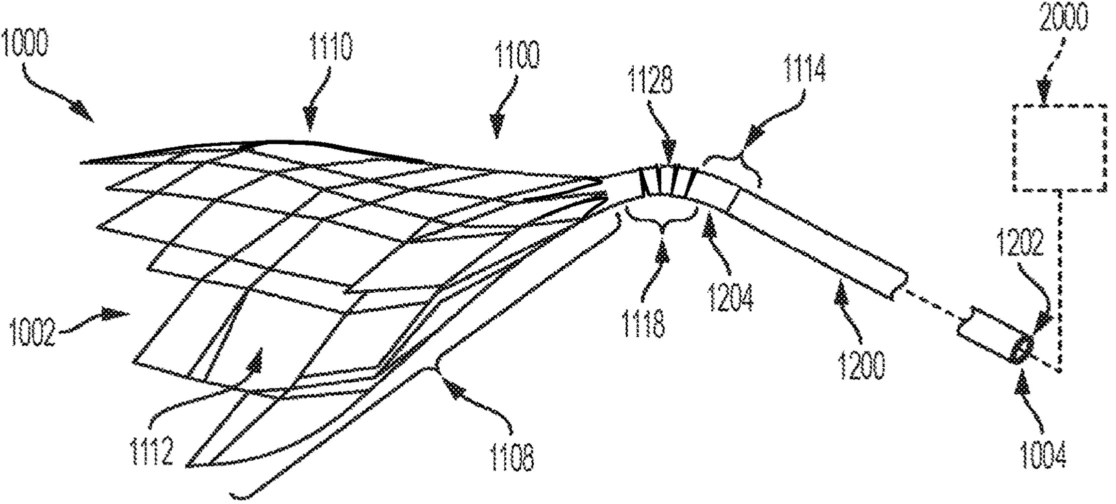
FIG. 1 is an illustration of an embolic filter system, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. In describing various examples, the term distal is used to denote a position along an exemplary device proximate to or alternatively nearest to the treatment area within a patient's body. The term proximal is used to denote a position along the exemplary device proximate to or alternatively nearest to the user or operator of the device.

Various aspects of the present disclosure are directed toward an embolic filter device, system, and method. An exemplary embolic filter system 1000 is illustrated in FIG. 1. The embolic filter system 1000 generally includes a filter 1100 and an elongate element 1200. In various examples, the embolic filter system 1000 is configured such that the filter 1100 and the elongate element 1200 can freely articulate relative to one another. As discussed in greater detail below, in some examples, the filter 1100 includes one or more features that facilitate such relative articulation between the filter 1100 and the elongate element 1200, while in other examples, the embolic filter system 1000 includes one or more additional components, such as one or more unions that facilitate such relative articulation between the filter 1100 and the elongate element 1200. Providing an embolic filter system 1000 having a filter 1100 and elongate element 1200 that are operable to articulate relative to one another provides that the embolic filter system 1000 can passively orient itself to achieve proper alignment of the filter 1100 relative to the vasculature within which it is partially or fully deployed. Alternatively, the embolic filter system 1000 can also be manipulated in situ by the operator to achieve such alignment.

As shown in FIG. 1, the embolic filter system 1000 includes a distal end 1002 and a proximal end 1004. In some examples, the filter 1100 extends distally from the elongate element 1200 such that a distal end 1102 of the filter 1100 defines, at least in part, the distal end 1002 of the embolic filter system 1000. Similarly, in some examples, the elongate element 1200 extends proximally from the filter 1100 such that a proximal end 1202 of the elongate element 1200 defines, at least in part, the proximal end 1004 of the embolic filter system 1000. In various examples, a proximal end 1104 of the filter 1100 is coupled with the elongate element 1200. In some examples, the proximal end 1104 of the filter 1100 is coupled with a distal end 1204 of the elongate element 1200. In some examples, coupling the proximal end 1104 of the filter 1100 with the distal end 1204 of the elongate element 1200 includes coupling the proximal end 1104 of the filter 1100 with the distal end 1204 of the elongate element 1200 such that the distal end 1204 of the elongate element 1200 is situated distal to the proximal end 1104 of the filter 1100 (e.g., such that the filter 1100 and the elongate element 1200 partially overlap one another).

In various examples, the embolic filter system 1000 can be used in combination with one or more auxiliary systems. For example, as shown in FIG. 1, one or more auxiliary systems 2000 including one or more auxiliary components may be utilized in combination with the embolic filter system 1000. In some examples, the auxiliary system 2000 and/or components thereof may be commercial-over-the-shelf (COTS) systems or components. One non-limiting auxiliary system 2000 includes a COTS catheter. Other non-limiting auxiliary systems 2000 include constraining sheaths, including tear-away sheaths, valves and connectors such as those used in controlling fluid backflow through one or more of the embolic filter system 1000 and the auxiliary system 2000 (e.g., Tuohy-Borst Connector(s)), and control handles. The auxiliary system 2000 may be used in association with one or more of the delivery, deployment, operation, and/or removal of the embolic filter system 1000. It is to be appreciated that, in various examples, the embolic filter system 1000 may, itself, include one or more of such tear-away sheaths, connectors, and/or valves, such as hemostatic valves.

The embolic filter system 1000 is generally configured to be advanced to a target site within a patient's vasculature such that one or more components of the embolic filter system 1000 (such as the filter 1100) is antegrade or "downstream" of a treatment area of the vasculature, between the treatment area and one or more anatomical regions where the presence of embolic debris can lead to complications and damage to the anatomy. Those of skill will appreciate that positioning the system downstream from the treatment area provides that embolic and other debris dislodged from the treatment area during a treatment procedure will migrate with the flow of blood toward the embolic filter system 1000 where the embolic debris can be filtered from the blood.

Properly orienting the filter 1100 of the embolic filter system 1000 within a vessel or region of the vasculature is an important factor in facilitating a proper deployment and successful filtering of embolic debris from the blood in association with an endovascular procedure. However, in certain portions of the vasculature and/or under certain conditions, it is difficult to deploy embolic filters such that they are operable to successfully filter embolic debris from the blood. The embolic filter system 1000 disclosed herein passively aligns itself along a surface of the vasculature such as a vessel wall to cause a relative articulation between the filter 1100 and the elongate element 1200, thus achieving a proper alignment of the filter 1100 within the vasculature. Alignment within the vasculature generally results in a minimization of gaps between the filter 1100 and the vessel wall that could operate as avenues through which the embolic debris can bypass the embolic filter system 1000. Though, in some embodiments, the embolic filter system 1000 also affords the operator the ability to deploy the embolic filter system 1000 and then manipulate the embolic filter system 1000 to properly align the filter 1100 with the vasculature.

In various examples, articulation is achieved by one or more of advancement and withdrawal of the elongate element 1200 with the filter 1100 fully deployed. For example, advancement and/or withdrawal of the elongate element 1200 while the filter 1100 is deployed within the vasculature may operate to impart a compressive or tensile load to one or more of the filter 1100 and the elongate element 1200. As mentioned above, in various examples, the filter 1100 may include one or more features that facilitate relative articulation between the filter 1100 and the elongate element 1200, while in other examples, the embolic filter system 1000 includes one or more additional components, such as one or more unions that facilitate relative articulation between the filter 1100 and the elongate element 1200. In various examples, applying compressive and/or tensile load(s), the embolic filter system 1000 causes the one or more features of the filter 1100 and/or the one or more additional components to bend, deflect, or otherwise cause deformation thereof to achieve the relative articulation between the filter 1100 and the elongate element 1200.

Once deployed, the embolic filter system 1000 interacts with blood flowing through the region of the vasculature within which the embolic filter system 1000 is deployed. In some examples, the embolic filter system 1000 may be adapted or otherwise configured to filter blood and/or embolic debris as it flows through or otherwise interacts with the embolic filter system 1000. In some examples, the embolic filter system 1000 additionally or alternatively redirects blood flow and/or embolic debris from what would otherwise be a normal or unimpeded flow of blood and/or embolic debris through the surrounding vasculature. Thus, in various examples, the embolic filter system 1000 can be deployed within a region of a patient's vasculature such that blood and/or embolic debris is filtered and/or redirected as it flows through that region of the patient's vasculature.

Figure 2:
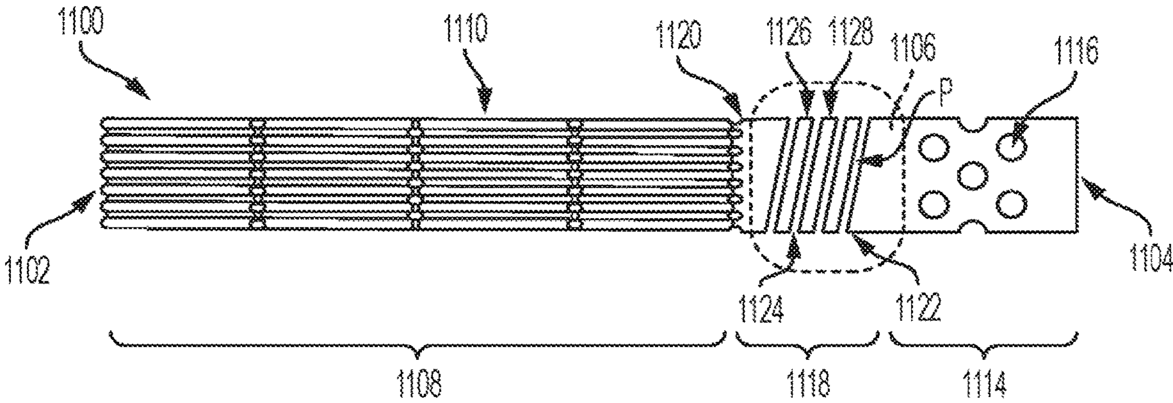
FIG. 2 is an illustration of a filter of an embolic filter system, according to some embodiments.

With reference now to FIGS. 1 and 2, the filter 1100 of the embolic filter system 1000 includes a body 1106 having the distal and proximal ends 1002 and 1004. The filter 1100 generally includes a structural element 1108, an attachment section 1114, and an articulation section 1118. In some examples, the articulation section 1118 is intermediate to the distal and proximal ends 1102 and 1104, and thus may be referred to as an intermediate section. FIG. 2 is a 2-dimensional plan view of the filter 1100 showing the full circumference of the filter 1100, which has been unwrapped and laid flat to illustrate the relationship between the structural element 1108, the attachment section 1114, and the articulation section 1118.

In various examples, the filter 1100 is a structure configured to interact with blood and/or embolic debris flowing through the patient's vasculature in the region within which the embolic filter system 1000 is deployed. As discussed in greater detail below, the filter 1100 or one or more portions thereof may be formed from a cut tube, a wire frame, a molded or extruded part, or a combination thereof. In some examples, one or more portions of the filter 1100 may be formed of a shape-memory material such as nitinol, such that the one or more portions thereof possess or exhibit self-expanding properties as would be appreciated by those of skill in the art. In other examples, however, one or more of the components of the filter 1100 may be formed from other resilient metals that may be expandable through the use of an expansion aid (such as a balloon). For example, one or more of the support elements may be formed from a polymer or a biocompatible metallic alloy such as stainless steel. In some examples, the filter 1100 or one or more portions thereof may be constructed of a durable elastomeric material, such as polyurethane or densified nylon.

As shown in FIGS. 1 and 2, the filter 1100 includes a structural element 1108. The structural element 1108 (also referred to herein as a capture section) is configured to direct or funnel blood and embolic debris into an interior region of the filter 1100 and, in some examples, the elongate element 1200. The structural element 1108, therefore, operates as an obstruction to the flow of blood that causes the blood to interact with the embolic filter system 1000 before flowing downstream of the embolic filter system 1000. In various examples, the structural element 1108 is configured to transition between a contracted configuration (e.g., FIG. 2) and an expanded configuration (e.g., FIG. 1) in conjunction with the embolic filter system 1000 transitioning from a delivery configuration to a deployed configuration such that the embolic filter system 1000 can be delivered endovascularly (e.g., at a small delivery profile), while possessing the capability of being deployed in situ to a larger deployed profile conducive for interrupting blood flow to filter embolic debris therefrom.

Figure 3:
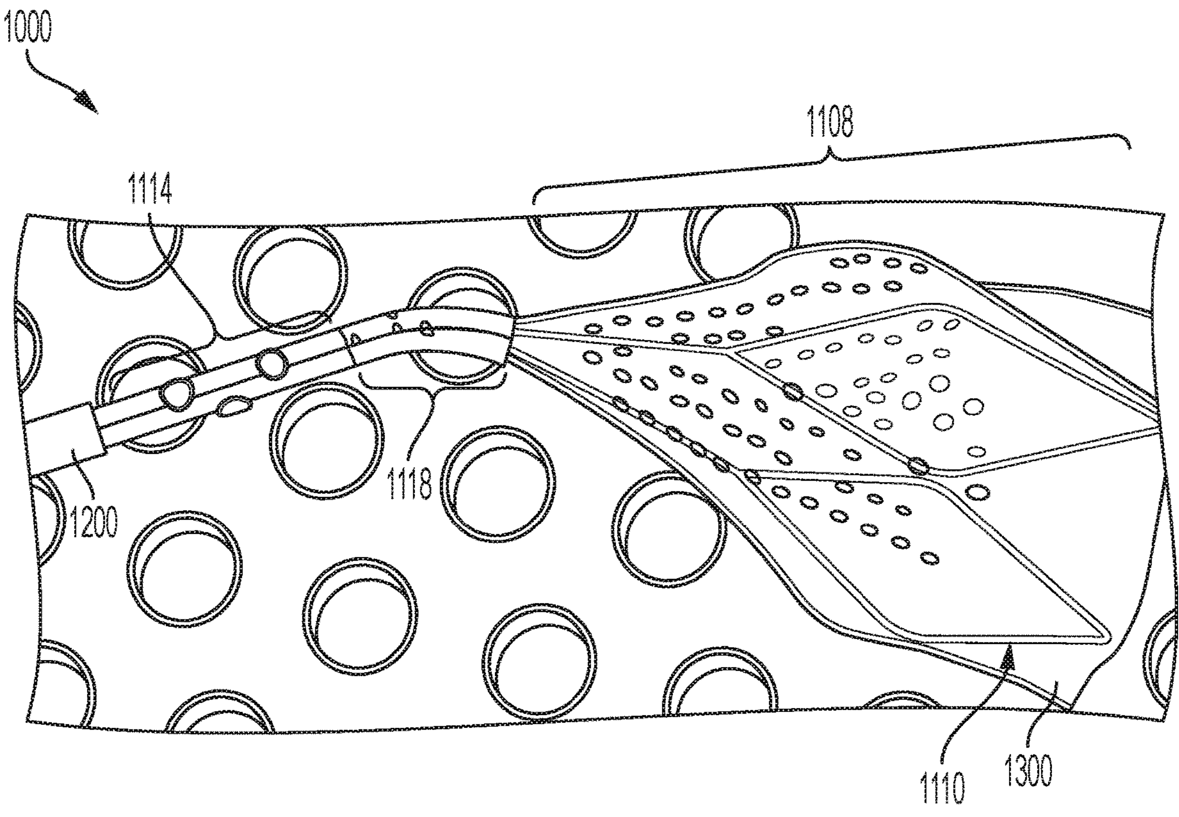
FIG. 3 is an illustration of an embolic filter system, according to some embodiments.

In the deployed configuration, the filter 1100 adopts a generally trumpeted, conical, or frustoconical shape in that a transverse cross-sectional area of the filter 1100 is different at two different longitudinal locations along the filter 1100 between the distal and proximal ends 1102 and 1104 of the filter 1100. In some examples, the transverse cross-sectional area of the distal end 1102 is greater than the transverse cross-sectional area of the proximal end 1104. In some examples, the filter 1100 generally tapers from the distal end 1102 to the proximal end 1104 as shown in FIGS. 1 and 3, for example. Such a configuration provides that the filter 1100 operates to funnel the blood into the filter 1100 and/or into the elongate element 1200 as disclosed herein.

In various examples, the structural element 1108 is comprised of one or more support elements, such as one or more braids, meshes, lattices, wires, rings, struts, or any other suitable support element. For example, as shown in FIGS. 1 and 2, the structural element 1108 includes a plurality of strut elements 1110 that are collectively arranged to define one or more closed cells 1112 that collectively define, at least in part, the structural element 1108. As shown, these closed cells 1112 are arranged in one or more rows (e.g., 1, 2, 3, 4, or more than 4 rows). It is to be appreciated, however, that braids, meshes, lattices, wires, rings, and other suitable support elements may be utilized in lieu of or in combination with the strut elements 1110, provided that the structural element 1108 of the filter 1100 is operable to transition between the contracted and expanded configurations.

In some examples, the closed cells 1112 are configured to change shape to accommodate or facilitate the transition of the structural element 1108 between the expanded and contracted configurations. When the structural element 1108 is in the expanded configuration, for example, the closed cells may be diamond-shaped as shown in FIG. 1. It will be appreciated, however, that the shape of the closed cells shown herein is not to be construed as limiting, and that various alternative shapes (e.g., polygonal) and/or sizes are envisioned.

It is also to be appreciated that the number of rows of closed cells and/or the number of closed cells per row may be increased or decreased to achieve a desired expanded profile (e.g., deployed diameter) and a desired contracted profile (e.g., delivery diameter), and thus the examples illustrated herein are not to be construed as limiting. Generally, for a given closed cell size and shape, increasing the number of closed cells 1112 increases the expanded and contracted profile diameters, and decreasing the number of closed cells 1112 decreases the expanded and contracted profile diameters. Similarly, for a given closed cell size and shape and number of closed cells 1112 per row, increasing the number of rows of closed cells 1112 increases a length of the filter 1100, and decreasing the number of rows of closed cells 1112 decreases the length of the filter 1100.

In various examples, in addition to the structural element 1108, the filter 1100 includes one or more portions that are configured to facilitate a coupling of the filter 1100 to the elongate element 1200. For example, as shown in FIGS. 1 and 2, the filter 1100 includes an attachment section 1114 that is configured to interface with the elongate element 1200 to facilitate a coupling between the filter 1100 and the elongate element 1200. The attachment section 1114 may include one or more features that are configured to help secure the elongate element 1200 to the attachment section 1114. For example, as shown in FIG. 2, the attachment section 1114 includes a plurality of apertures 1116. The apertures 1116 provide reliefs within which the material of the elongate element 1200 can reside to facilitate a mechanical interference between the filter 1100 and the elongate element 1200. For instance, the elongate element 1200 may be coupled with the filter 1100 via melt-bonding or other known methods. For instance, the elongate element 1200 may be coupled with the filter 1100 using an adhesive such as an ultraviolet light (UV) curing adhesive (for example a UV curable acrylate), an epoxy, a fluoroelastomer (e.g., FEP), a fluoropolymer adhesive tape, or other means as desired.

It is to be appreciated that while the attachment section 1114 of the filter 1100 is shown with apertures 1116, the attachment section 1114 may additionally or alternatively include one or more other features configured to assist in coupling the elongate element 1200 with the filter 1100, such as one or more projections (e.g., one or more boss features) extending circumferentially or about an interior or exterior of the attachment section 1114 of the filter 1100 and/or extending longitudinally along the interior or exterior of the attachment section 1114. In some such examples, such features may be welded or otherwise affixed to the filter according to known methods.

In various embodiments, situated between the structural element 1108 and the attachment section 1114, is an articulation section 1118 that is adapted to enable the structural element 1108 (e.g., the capture section) and the attachment section 1114 of the filter 1100 to articulate relative to one another. Such relative articulation provides that the structural element 1108 is operable to articulate relative to the elongate element 1200 (and vice versa). While the embolic filter system 1000 shown in FIGS. 1 and 2 includes a filter 1100 with an articulation section 1118 integrated therein (e.g., situated between the distal and proximal ends 1102 and 1104 of the filter 1100), it should be appreciated that, as discussed in greater detail below, an articulation section may additionally or alternatively be situated between a filter and an elongate element. That is, the articulation section may be included in an embolic filter system as an independent component that is coupled with each of the filter and the elongate element.

In various examples, the articulation section 1118 includes a distal section 1120 and a proximal section 1122 and has a length. In some examples, the distal section 1120 defines a position along the filter 1100 at which the articulation section 1118 transitions to the structural element 1108. Similarly, in some examples, the proximal section 1122 defines a position along the filter 1100 at which the articulation section 1118 transitions to the attachment section 1114.

In various embodiments, the articulation section 1118 generally includes a coil (e.g., a helical construct) or a slotted segment of the filter 1100. In the examples including a cut tube, it is to be appreciated that the cuts in the tube to form the coil/helix or slotted segment extend through the thickness of the tube (e.g., from an exterior surface of the tube to the interior surface of the tube) such that the interior lumen of the tube is exposed. Cutting through the full thickness of the tube in such examples provides that one or more compressible/expandable gaps are formed, as discussed further below. The tube may be formed of resilient materials including, but not limited to, metal alloys (e.g., nitinol), polymeric and elastomeric materials, or a combination thereon. For instance, the articulation section 1118 may include nylon that is reinforced with a coil of reinforcing material.

In various examples, the particular aspects or features of the articulation section 1118 (e.g., the pitch of the helix or the size of the slots and distance therebetween) is selected to provide that the structural element 1108 and one or more of the attachment section 1114 and the elongate element 1200 can be articulated relative to one another by a designated amount. For instance, the particular aspects or features of the articulation section 1118 (such as the pitch "p") can be configured such that the structural element 1108 and one or more of the attachment section 1114 and the elongate element 1200 can be articulated such that a relative angle defined between the longitudinal axes thereof (i.e., an articulation angle) is up to 30 degrees, up to 45 degrees, up to 60 degrees, up to 90 degrees, up to 180 degrees, up to 270 degrees, or in excess of 270 degrees, such as up to 360 degrees. These relative angles are not intended to be limiting but are instead intended to be exemplary. For instance, the articulation section 1118 can be configured to adopt an articulation angle of up to between 90 and 180 degrees, or up to between 180 and 270. Additionally or alternatively, in some examples, a length of the articulation section 1118 can be varied to increase, decrease, or otherwise alter the number, shape, and configuration of the particular aspects or features facilitating articulation (e.g., no. of coils, helix pitch, slot width), and thereby alter the degree of passive articulation. For instance, an articulation section having a first quantity of helical coils arranged at a first pitch may provide a first degree of articulation, while an articulation section having a second quantity of helical coils arranged at the first pitch facilitates a second, greater degree of articulation. In various implementations, pitch values may range from 0 degrees to 90 degrees for example, although a variety of angles are contemplated.

In various examples, the coil/helical or slotted pattern can be cut into a tube to form the articulation section 1118. Alternatively, the coil/helical or slotted pattern can be formed or molded, as discussed herein. Adapting the articulation section 1118 to bend, deflect, or otherwise deform provides that the articulation section 1118 is transitionable between a generally linear state and a generally curved state. In various examples, the generally linear state is a steady state configuration of the articulation section 1118, where the articulation section 1118 is not influenced to curve as a result of some external force acting on the system.

Configuring the articulation section 1118 with one or more of a coil/helical or slotted cut pattern provides that one or more gaps or spaces exist between adjacent helical windings or adjacent slots. For instance, as shown in FIG. 2, the gap 1124 between the first helical winding 1126 and the second helical winding 1128 (e.g., adjacent helical windings) provides that the articulation section 1118 can adopt a curvature, whereby the gap 1124 in a first region of the helical winding (e.g., at a first angular position) is reduced in conjunction with the gap 1124 in a second region of the helical winding (e.g., at a second angular position 180 degrees offset from the first angular position) is maintained or increased. Those of skill in the art should also appreciate that the decrease and/or increase in gap space is attributable, at least in part, to a deformation (e.g., bending) of one or more of the helical windings (e.g., 1126 and 1128). In some examples, the articulation section 1118 comprising the coil/helical or slotted pattern may be covered under at least one layer of flexible polymer such as a fluoropolymer material (e.g., an expanded polytetrafluoroethylene ("ePTFE"), expanded modified PTFE, or expanded copolymers of PTFE), nylons, polycarbonates, polyethylenes, polypropylenes, combinations of any of the foregoing, or other materials.

In various examples, the articulation section 1118 may be configured to elastically deform under normal operating conditions (e.g., where the articulation section 1118 is configured to elastically deform to accommodate a maximum expected articulation during a given endovascular procedure). By configuring the articulation section 1118 to elastically deform under expected operating conditions (e.g., an expected degree of angulation), the embolic filter system provides that the filter 1100 can be articulated relative to the elongate element 1200 in a resilient manner such that the articulation section 1118 resiliently returns to its linear state upon removal of the force required to cause the articulation. Such a configuration provides that the embolic filter system 1000 is in linear alignment for collapse and removal following an endovascular procedure.

In other examples, the articulation section 1118 may be configured to at least partially plastically deform under normal operating conditions (e.g., where the articulation section 1118 is configured to at least partially deform to accommodate an expected articulation during a given endovascular procedure). By configuring the articulation section 1118 to plastically deform under expected operating conditions (e.g., an expected degree of angulation), the embolic filter system provides that the filter 1100 can be articulated relative to the elongate element 1200 in a non-resilient manner such that a degree of angulation required can be established, whereby the operator is not required to continue inputting force to the elongate element 1200 to maintain the desired relative articulation. Thus, a force can be input to the elongate element 1200 to cause a desired degree of relative angulation between the filter 1100 and the elongate element 1200, whereby the relative angulation is maintained as a result of plastic deformation of at least the articulation section 1118 of the filter 1100. In some such examples, withdrawal of the embolic filter system 1000 into a constraining catheter following an endovascular procedure causes the articulation section 1118 to straighten, thereby causing re-alignment of the structural element 1108 with the elongate element 1200 for removal, such as through a catheter.

As mentioned above, the filter 1100 may include one or more shape memory alloys, and thus may include one or more sections that are expandable. Thus, in various embodiments, the filter 1100 is configured to transition between a delivery configuration and a deployed configuration, where one portion of the filter 1100 is expanded relative to another portion of the filter 1100. For instance, in the delivery configuration, each of the various sections (e.g., the structural element 1108, the articulation section 1118, and the attachment section 1114) of the filter 1100 exhibit a profile (e.g., a diameter) adapted for delivery through a patient's vasculature, such as through or within a delivery catheter as described further below. Conversely, in the deployed configuration, one or more of the various sections of the filter 1100 are expanded relative to one or more of the other various sections of the filter 1100. As shown in FIG. 1, the embolic filter system 1000 is shown in a deployed configuration, where the structural element 1108 is expanded relative to each of the articulation section 1118, the attachment section 1114, and the elongate element 1200. In some examples, the filter 1100 is configured such that the structural element 1108 is self-expandable. In other examples, however, the filter 1100 is configured such that the structural element 1108 is expandable through the use of an expansion aid (such as a balloon).

In various examples, the elongate element 1200 is a longitudinally extending structure having a proximal end 1202 and a distal end 1204. In some examples, the elongate element 1200 is configured to receive blood and/or embolic debris that is directed into the embolic filter system 1000 by the filter 1100. Accordingly, in some examples, the elongate element 1200 includes a lumen. In various examples, the elongate element 1200 is configured to be advanceable through the vasculature. Thus, the elongate element 1200 is generally flexible yet longitudinally stable and compressible without risk of kinking or buckling under loading conditions consistent with advancement through vasculature, including advancement through one or more delivery catheters. In some examples, the elongate member 1200 may include a braided, wrapped, or cut reinforcement member attached to a body portion of the elongate member 1200 as a framework to add stability to the structure of the elongate member 1200. A reinforcement member may be braided by weaving a plurality of wire strands made of a suitable material. Regardless, the reinforcement member (e.g., the wire(s) or filament(s) forming the reinforcement member) may be made of metal and metal alloys (e.g., nitinol), polymeric materials, elastomeric materials, natural materials, or combinations of any of the foregoing. The reinforcement member may be symmetrically braided (e.g. with an opposing bias in an over/under configuration to form a typical braid) or having an asymmetric bias, with each strand of the braided wire oriented at a pitch angle ranging from 0° to 10°, 10° to 20°, 20° to 30°, 30° to 40°, 40° to 50°, 50° to 60°, 60° to 70°, 70° to 80°, 80° to 90°, or any combination thereof, relative to a longitudinal axis of the braided wire.

The elongate element 1200 may therefore comprise various materials including but not limited to medical grade polymeric materials including thermoplastic polymers, organosilicon polymers, and polyamides. Polyether block amide (e.g., PEBAX®), Nylon, polytetrafluoroethylene (PTFE), and Stainless steel are suitable non-limiting examples. The elongate element 1200 may be formed according to known methods, such as extrusion. In some examples, the elongate element 1200 may include one or more reinforcement elements, such as one or more fibers or braids extending along or within the material of the elongate element 1200. For instance, in some examples, the elongate element 1200 may include coil reinforced Nylon or PEBAX.

In some examples, the elongate element 1200 may be formed using a high durometer material, in which the hardness of the elongate element 1200 may be from 50 to 60 Shore Hardness Units, 60 to 70 Shore Hardness Units, 70 to 80 Shore Hardness Units, 80 to 90 Shore Hardness Units, or any combination thereof. Such materials may include thermoplastics, for example but not limited to Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Polycarbonate (PC), Polyphenylene Oxide (PPO), Modified Polyphenylene Oxide (Mod PPO), Polyphenylene Ether (PPE), Modified Polyphenylene Ether (Mod PPE), Thermoplastic Polyurethane (TPU); Polyamides such as nylon-11 and nylon-12, Polyoxymethylene (POM or Acetal), Polyethylene Terephthalate (PET, Thermoplastic Polyester), Polybutylene Terephthalate (PBT, Thermoplastic Polyester), Polyimide (PI, Imidized Plastic), Polyamide Imide (PAI, Imidized Plastic), Polybenzimidazole (PBI, Imidized Plastic); Polysulfone (PSU), Polyetherimide (PEI), Polyether Sulfone (PES), Polyaryl Sulfone (PAS); Polyphenylene Sulfide (PPS), Polyetheretherketone (PEEK); Fluoropolymers that include Fluorinated Ethylene Propylene (FEP), Ethylene Chlorotrifluoroethylene (ECTFE), Ethylene, Ethylene Tetrafluoroethylene (ETFE), Polychlorotrifluoroethylene (PCTFE), Polyvinylidene Fluoride (PVDF), Perfluoroalkoxy (PFA), or combinations, copolymers, or derivatives thereof. Other commonly known medical grade materials include elastomeric organosilicon polymers and polyether block amide. In particular, polyamides can include nylon 12, nylon 11, nylon 9, nylon 6/9, and nylon 6/6. In certain embodiments, PET, nylon, and PE may be selected for medical balloons used in high pressure applications. In some embodiments, the elongate element 1200 may include a braid reinforced structure to improve burst pressure resistance. In some embodiments, the elongate element 1200 may include one or more layers of hydrophilic coatings or other types of low-friction coatings and/or liners to reduce friction forces on the surface thereof. The specific choice of materials depends on the desired characteristics or intended application of the balloon.

The aforementioned reinforcement member may be combined with the high durometer material to form the elongate element 1200 such that the body portion of the elongate element 1200 is reinforced while the end of the elongate element 1200 is inserted into the proximal end 1104 of the filter 1100. In some examples, the high durometer material helps facilitate bonding of the end of the elongate element 1200 to the proximal end 1104 (e.g., by facilitating greater flow and mechanical engagement during heating and/or by increasing frictional/stiction engagement). In some examples, the bonding may be assisted using an adhesive, such as the UV cured adhesive as previously explained.

In some examples, blood and/or embolic debris entering the elongate element 1200 flows through the lumen of the elongate element 1200, such as from the distal end 1204 of the elongate element 1200 to the proximal end 1202 of the elongate element 1200. In some examples, one or more auxiliary systems 2000 may be fluidly coupled with the lumen of the elongate element 1200, such as at the proximal end 1202 of the elongate element 1200. In some such examples, such auxiliary systems 2000 may be operable to aspirate the contents of the lumen (e.g., embolic debris and/or blood) of the elongate element 1200.

In some examples, the lumen of the elongate element 1200 forms a working lumen through which one or more medical devices (e.g., guidewires, endoprostheses) can be passed to treatment areas proximate the embolic filter system 1000. Thus, in various examples, the lumen of the elongate element 1200 operates as both a working lumen for medical device delivery as well as a structure for redirecting the flow embolic debris and/or blood. In some examples, the working lumen of the elongate element 1200 may be in a range of 4 Fr to 26 Fr, or larger.

Examples of medical devices that may be passed through the lumen of the elongate element 1200 include but are not limited to catheters, thrombectomy devices, atherectomy devices, embolectomy devices, and tools associated therewith, contrasting agents, drug delivery agents, endovascular prostheses including stents, stent-grafts, and valves, for example.

In various embodiments, the embolic filter system 1000 includes a membrane disposed along one or more portions of the filter 1100, and optionally along one or more portions of the elongate element 1200. For example, as shown in FIG. 3, a membrane 1300 is disposed about an exterior of the structural element 1108 and the articulation section 1118 of the filter 1100. In these examples, by disposing the membrane 1300 along the articulation section 1118 and the structural element 1108, the membrane 1300 operates to filter and retain embolic debris within the embolic filter system 1000 that would otherwise be free to escape through the voids in the structural element 1108 (e.g., the closed cells 1112) and the articulation section 1118 (e.g., the gaps 1124). Accordingly, a configuration with the membrane 1300 in combination with an articulation section (e.g., articulation section 1118) whose internal lumen is exposed is one that is operable to filter embolic debris from the blood while maintaining the ability to freely articulate the elongate element 1200 relative to the filter 1100 (and vice versa). In some examples, the portion of the membrane 1300 extending along the articulation section 1118 is blood impermeable.

Under certain conditions, the forces required to withdraw the embolic filter system 1000 from the vasculature may be quite high (e.g., higher than the forces required to cause the articulation section 1118 to bend to facilitate articulation between the filter 1100 and the elongate element 1200). For instance, removal of the embolic filter system 1000 may include withdrawing the embolic filter system 1000 within a delivery catheter, which includes re-collapsing the deployed filter 1100 whereby the distal end of the delivery catheter operates as a bearing surface that causes the filter 1100 to radially collapse as the embolic filter system 1000 is withdrawn into a lumen of the delivery catheter. As such, disposing a membrane 1300 about the articulation section 1118 operates to increase a tensile strength of the articulation section 1118. That is, a tensile strength of the combined membrane 1300 and helically shaped/slotted material of the filter 1100 exceeds the tensile strength of the helically shaped/slotted material of the filter 1100. And, while increasing the tensile strength of the articulation section 1118 bears with it an ancillary effect of modifying the flexibility of the articulation section 1118 (e.g., the degree to which the articulation section 1118 can bend or articulate), such can be done while maintaining a sufficient degree of flexibility in the articulation section 1118 to facilitate the desired degree of articulation between the filter 1100 and the elongate element 1200.

It should be appreciated that the membrane 1300 may additionally or alternatively be disposed about an interior of the structural element 1108 and the articulation section 1118. In some examples, the membrane 1300 may optionally extend to cover a portion of the overlapping sections of the elongate element 1200 and attachment section 1114 of the filter 1100.

In some examples, the membrane 1300 operates to filter or otherwise condition the blood and embolic debris flowing into the embolic filter system 1000. In some examples, the membrane 1300 is permeable to certain blood media (e.g., blood-permeable) and impermeable to certain other blood media and/or embolic debris. Specifically, in some examples, the membrane 1300 is configured such that certain blood media (e.g., red blood cells, white blood cells, plasma, platelets, etc.) flowing into the embolic filter system 1000 can permeate the membrane 1300 of the filter 1100 and re-enter the vasculature while the membrane 1300 is impermeable to certain other blood media and embolic debris. In some examples, the membrane 1300 is impermeable to embolic debris of a designated size or larger. That is, in some examples, the membrane 1300 operates to obstruct embolic debris of a designated size or larger from permeating the membrane 1300 of the filter 1100 and re-entering the vasculature.

In some examples, the blood media and embolic debris flowing into the embolic filter system 1000 that does not permeate back into the vasculature is either captured and retained within the filter 1100 or is further directed into the elongate element 1200. In some examples, as explained in greater detail below, the filter 1100 is collapsible such that blood media and embolic debris captured within the filter 1100 can be subsequently removed with the removal of the embolic filter system 1000 from the vasculature.

In some examples, blood and/or embolic debris that is directed into the elongate element 1200 may be aspirated therefrom prior to removal of the embolic filter system 1000 from the vasculature. Evacuating embolic debris that is captured within the filter 1100 helps minimize the risk that the captured embolic debris will be unintentionally released back into the patient's vasculature during removal of the embolic filter system 1000 from the patient's vasculature. For example, a known risk during embolic debris filtering procedures is the risk of tearing the membrane 1300 of the filter 1100 during removal. Embolic filters that are filled with embolic debris generally occupy a larger cross-sectional area than do embolic filters free of embolic debris. This increased cross section can be associated with difficultly in sufficiently collapsing the embolic filter to a configuration wherein the embolic filter can be completely retracted within a delivery catheter. Even where the filter is not retracted within a delivery catheter, withdrawing a filter having a larger diameter as a result of being filled with embolic debris through tortuous vasculature can be difficult.

The membrane 1300 may comprise various materials including, but not limited to polymers such as fluoropolymers like an expanded polytetrafluoroethylene ("ePTFE"), expanded modified PTFE, expanded copolymers of PTFE, FEP, PFA, nylons, polyurethanes, polycarbonates, polyethylenes, polyester, silicone and silicone elastomers (e.g. SYLGARD™ 184), urethane, thermoplastic polyurethane, polypropylenes, and the like.

In various examples, one or more regions of such materials may be further or alternatively modified by forming one or more perforations therein to control the permeability of the material. For example, a material such as an expanded fluoropolymer (or another suitable polymer) can be further modified by perforating one or more regions of the material to achieve a designated porosity. Examples include laser cutting or laser drilling holes or perforations into a material. Other materials having a woven, knitted or lattice configuration may also serve as adequate materials based on their permeability/porosity. Moreover, a desired permeability may be achieved through increasing or decreasing layers of the membrane material, as those of skill will appreciate. Additionally or alternatively, the permeability of the membrane 1300 may be optimized by manipulating the microstructure of the membrane material. In some such instances, a node and fibril configuration of an expanded fluoropolymer can be modified/optimized to achieve desired permeability. For example, an expanded fluoropolymer can be processed such that a node and fibril configuration of the expanded fluoropolymer is generally impermeable to embolic debris (and other blood media) of a designated size consistent with the discussion below.

In some examples, the membrane material can be configured such that one or more portions or regions are permeable to a media up to a designated size while one or more other portions or regions are impermeable to the media of the designated size or larger. In some examples, the size of the pores or perforations (or voids in the node and fibril microstructure) present in the membrane material may vary, for example, from a proximal end to a distal end and/or at one or more discrete locations.

In various examples, the membrane 1300 may be configured such that the membrane 1300 is impermeable to embolic debris greater than or equal to about 140 μm. In some such examples, the average pore size (or perforation size or void size in the node and fibril microstructure of the membrane 1300) may be less than 140 μm. In other examples, the membrane 1300 may be configured such that the membrane is impermeable to embolic debris smaller than 140 μm, such as embolic debris in the range of 40 μm to 99 μm. Such examples are not intended to be limiting. For instance, if desired, the membrane 1300 may be configured to be permeable to embolic debris of 100 μm, 120 μm, 140 μm, 160 μm, 180 μm, 200 μm (or larger), and anywhere therebetween, in which case an average pore size (or perforation size or void size in the node and fibril microstructure of the membrane 1300) may exceed 150 μm.

In various embodiments, the embolic filter system 1000 is advanced to the treatment area within the vasculature in a delivery configuration, after which the embolic filter system 1000 is operable to be deployed or otherwise transitioned to a deployed configuration. In the delivery configuration, the embolic filter system 1000 is in a generally contracted configuration. In some examples, in the delivery configuration, the structural element 1108 is radially contracted such that the structural element 1108 is operable to be delivered endovascularly (e.g., at a small delivery profile), such as through a delivery catheter as discussed further below. In some examples, one or more of the articulation section 1118, the attachment section 1114, and one or more regions of the elongate element 1200 may additionally be radially contracted, though the same is not required. In the deployed configuration, the structural element 1108 is transitioned to a radially expanded configuration (e.g., FIG. 1) operable to interrupt blood flow to cause embolic debris to be filtered therefrom. In some examples, one or more of the articulation section 1118, the attachment section 1114, and one or more regions of the elongate element 1200 may additionally be radially expanded in the delivery configuration, though the same is not required.

After completion of the endovascular procedure, the embolic filter system 1000 is operable to be removed from the vasculature. In some examples, embolic debris captured by the embolic filter system 1000 may be aspirated or otherwise removed from the embolic filter system 1000 prior to removal of the embolic filter system 1000 from the vasculature, as mentioned herein. In some examples, to remove the embolic filter system 1000, the embolic filter system 1000 is transitioned from the deployed configuration to the delivery configuration. In some examples, such a transition from the deployed configuration to the delivery configuration includes a contraction of one or more portions of the embolic filter system 1000 (e.g., one or more portions of the filter 1100 and the elongate element 1200). For instance, in various examples, removal of the embolic filter system 1000 includes radially contracting or compressing the structural element 1108 of the filter 1100 to a profile (e.g., a diameter) conducive for endovascular removal. It is to be appreciated that a diameter of the structural element 1108 is smaller when the embolic filter system 1000 is in the delivery configuration that when the embolic filter system 1000 is in the deployed configuration.

The embolic filter system 1000 is operable to be delivered to treatment areas within the vasculature in association with a variety of different delivery methods. As such, the embolic filter system 1000 is also operable to be assembled in a variety of different methods. The following discussion details various assembly and delivery methods associated with the embolic filter system 1000.

Figure 4:
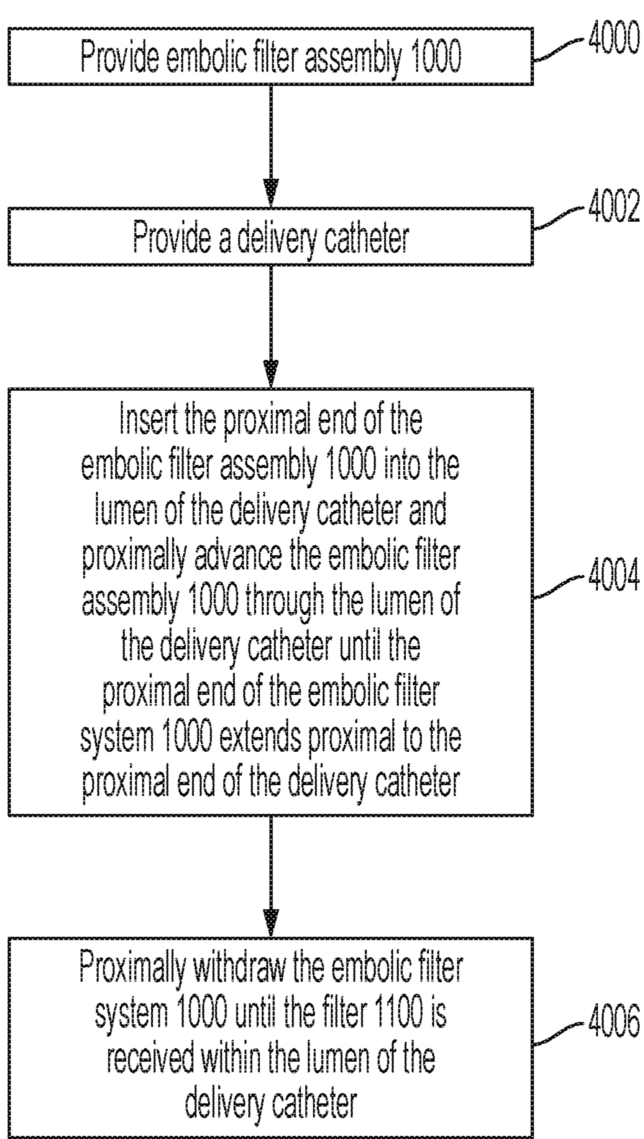
FIG. 4 is a flow chart of a method of assembling an embolic filter system, according to some embodiments.
Figure 5A:
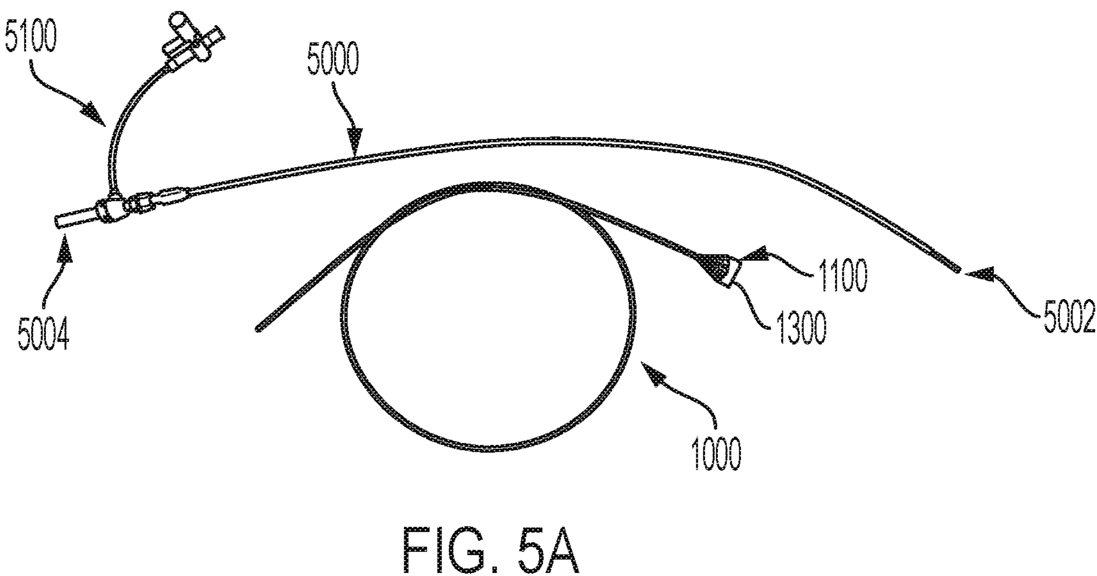
FIGS. 5A to 5D are illustrations of a method of assembling an embolic filter system, according to some embodiments.

Turning now to FIG. 4, a flow chart is illustrated that outlines one example method for a medical device assembly including the embolic filter system 1000. As shown, step 4000 includes providing the embolic filter system 1000. As discussed above, the embolic filter assembly generally includes a filter 1100 coupled with an elongate element 1200, wherein a membrane 1300 extends along one or more portions of the filter 1100 and optionally along one or more portions of the elongate element 1200. Step 4002 includes providing a delivery catheter. In various examples, the delivery catheter may be a COTS delivery catheter, consistent with the discussion above. In various examples, the delivery catheter therefore includes an elongate element having a distal end and a proximal end, and a lumen extending therethrough from the proximal end to the distal end. A COTS delivery catheter 5000 is shown in FIG. 5A, along with the embolic filter system 1000, including the filter 1100, the elongate element 1200, and the membrane 1300. The COTS delivery catheter 5000 may optionally include one or more connectors, such as connector 5100, which may include a hemostasis valve or other element. It should be appreciated that the embolic filter system 1000 is shown in FIG. 5A coiled up in a packaging configuration. As such, it will be appreciated that the embolic filter system 1000 will be uncoiled prior to use.

Figure 5B:
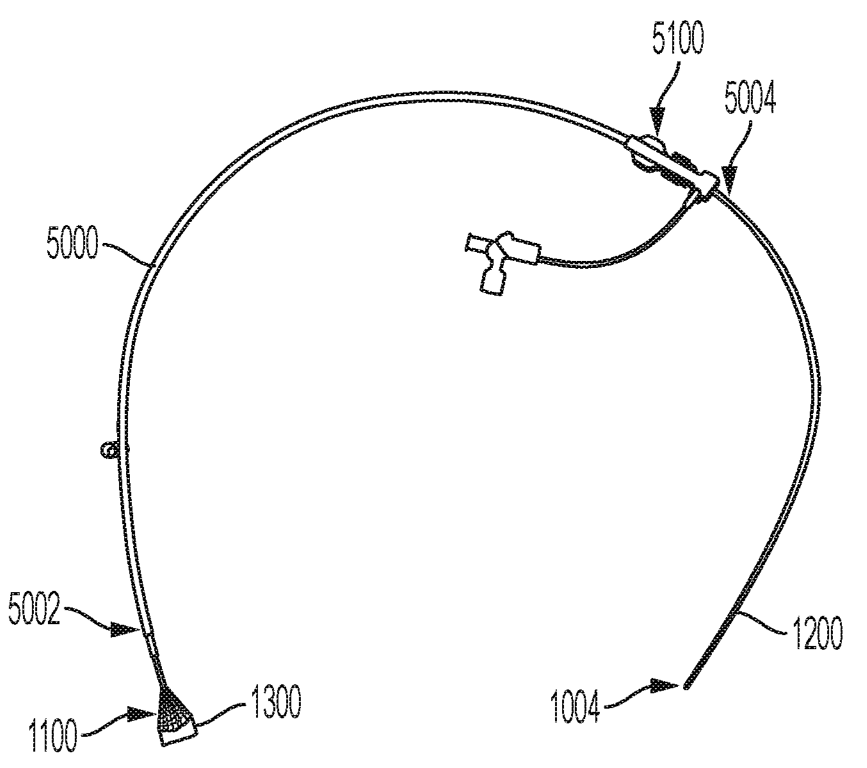

Turning back now to FIG. 4, at step 4004, the proximal end of the embolic filter system 1000 is inserted into the lumen of the delivery catheter and proximally advanced through the lumen of the delivery catheter until the proximal end of the embolic filter system 1000 extends proximal to the proximal end of the delivery catheter. For example, as shown in FIG. 5B, the proximal end 1004 of the embolic filter system 1000 has been inserted into the lumen of the delivery catheter 5000 at the distal end 5002 of the delivery catheter 5000 and proximally advanced through the lumen of the delivery catheter 5000 until the proximal end 1004 of the embolic filter system 1000 extends proximal to the proximal end 5004 of the delivery catheter 5000.

Figure 5C:
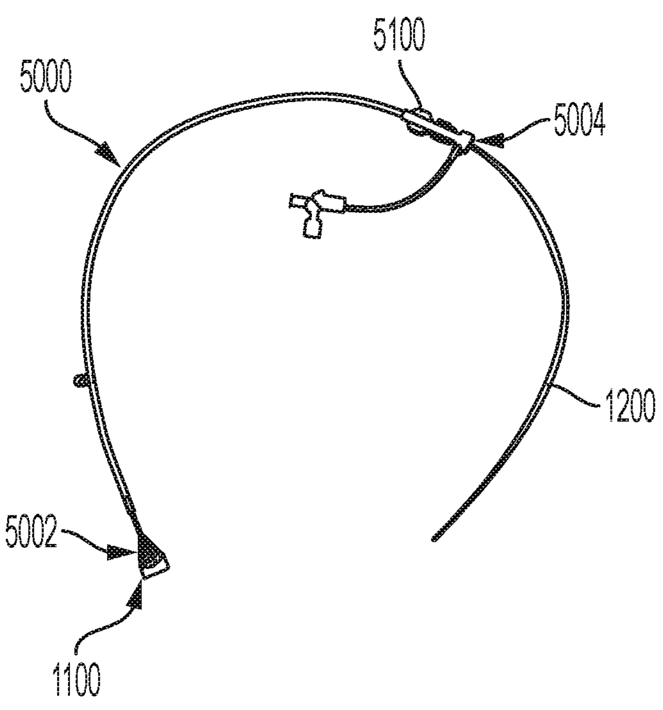
Figure 5D:
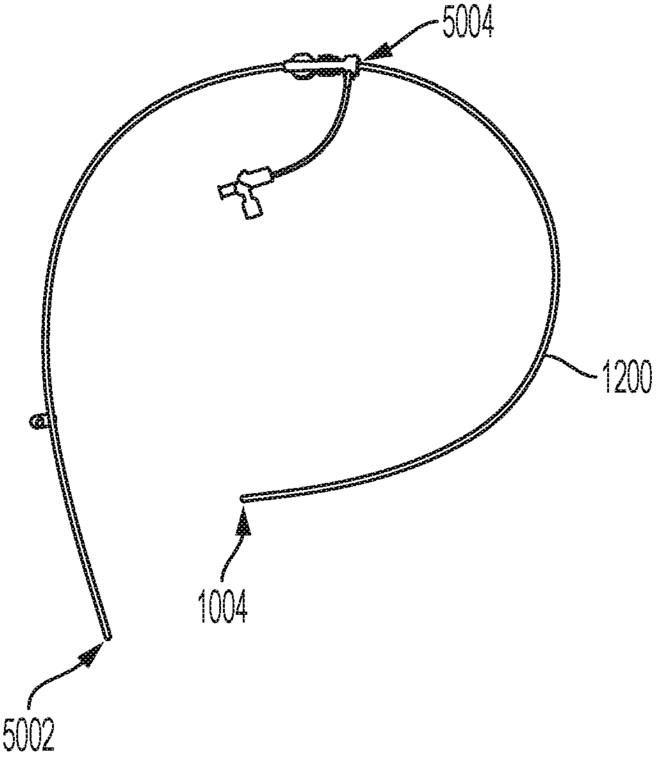

Turning back now to FIG. 4, at step 4006, the embolic filter system 1000 is proximally withdrawn until the filter 1100 is received within the lumen of the delivery catheter 5000. FIGS. 5C and 5D illustrate the proximal withdrawal of the embolic filter system 1000 relative to the delivery catheter 5000, where the embolic filter system 1000 is withdrawn such that the filter 1100 is partially received within the lumen of the delivery catheter 5000 in FIG. 5C, and where the embolic filter system 1000 is withdrawn such that the filter 1100 is completely received within the lumen of the delivery catheter 5000 in FIG. 5D.

Figure 5E:
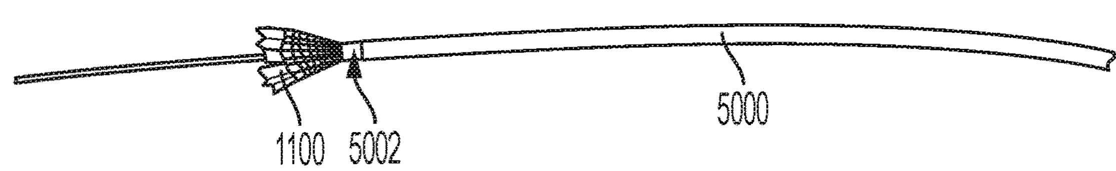
FIG. 5E to 5F are illustrations of a method of deploying an embolic filter system, according to some embodiments.
Figure 5F:

With the filter 1100 completely received within the lumen of the delivery catheter 5000, as shown in FIG. 5D, the delivery catheter 5000 can be inserted into the vasculature of a patient and advanced to a treatment site therein, whereinafter the embolic filter system 1000 can be advanced relative to the delivery catheter 5000 (e.g., by one or more of distally advancing the embolic filter system 1000 relative to the delivery catheter 5000 and proximally withdrawing the delivery catheter 5000 relative to the embolic filter system 1000) such that the filter 1100 extends distally from the distal end 5002 of the delivery catheter 5000. In some examples, as mentioned above, one or more portions of the filter 1100, such as the structural element 1108, are configured to radially expand to interrupt blood flow to filter embolic debris therefrom. For example, shown in FIGS. 5E and 5F is the embolic filter system 1000 being advanced distally relative to the delivery catheter 5000 such that the filter 1100 extends from the distal end 5002 of the delivery catheter 5000. FIG. 5E shows a portion of the filter 1100 extending from the distal end 5002 of the delivery catheter 5000, and partially deployed (e.g., radially expanded), and FIG. 5F shows the filter 1100 extending from the distal end 5002 of the delivery catheter 5000, fully deployed (radially expanded). It will be appreciated that FIGS. 5E and 5F are shown with the embolic filter system 1000 and delivery catheter 5000 outside of the body for clarity.

Figure 6:
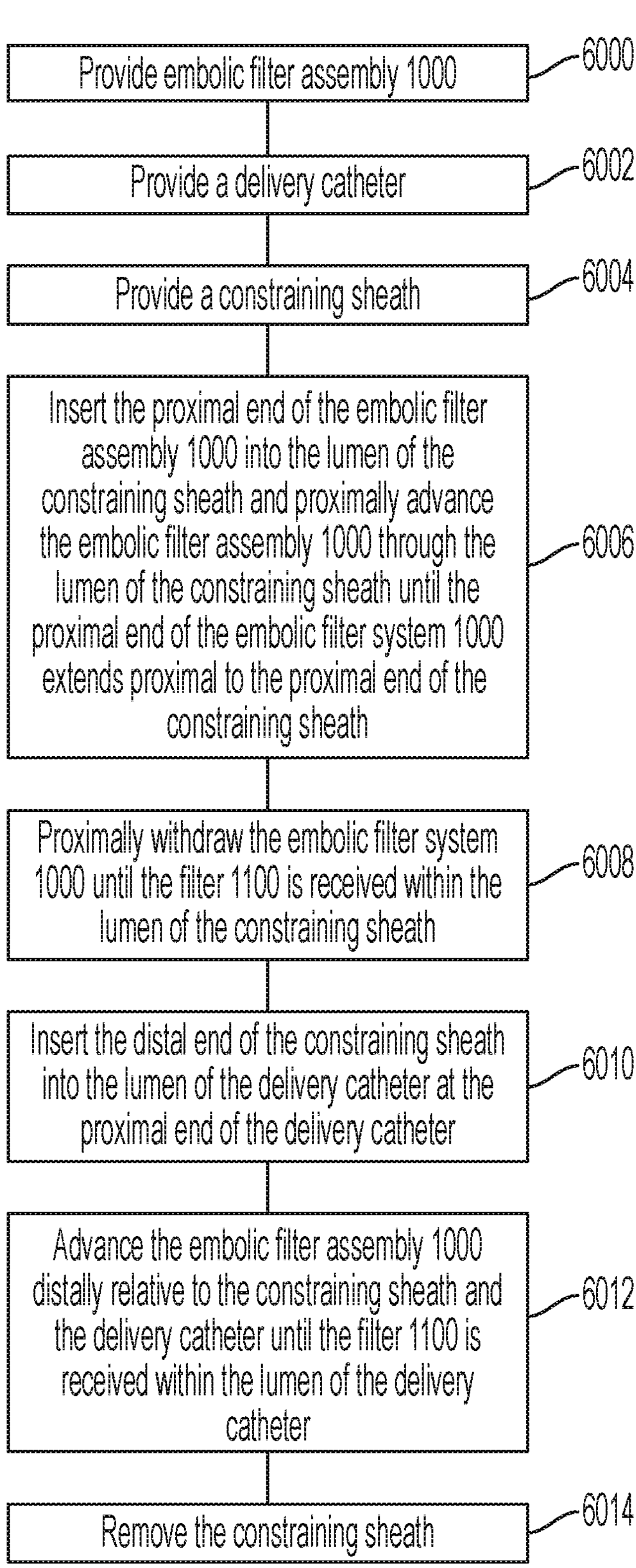
FIG. 6 is a flow chart of a method of assembling an embolic filter system, according to some embodiments.
Figure 7A:
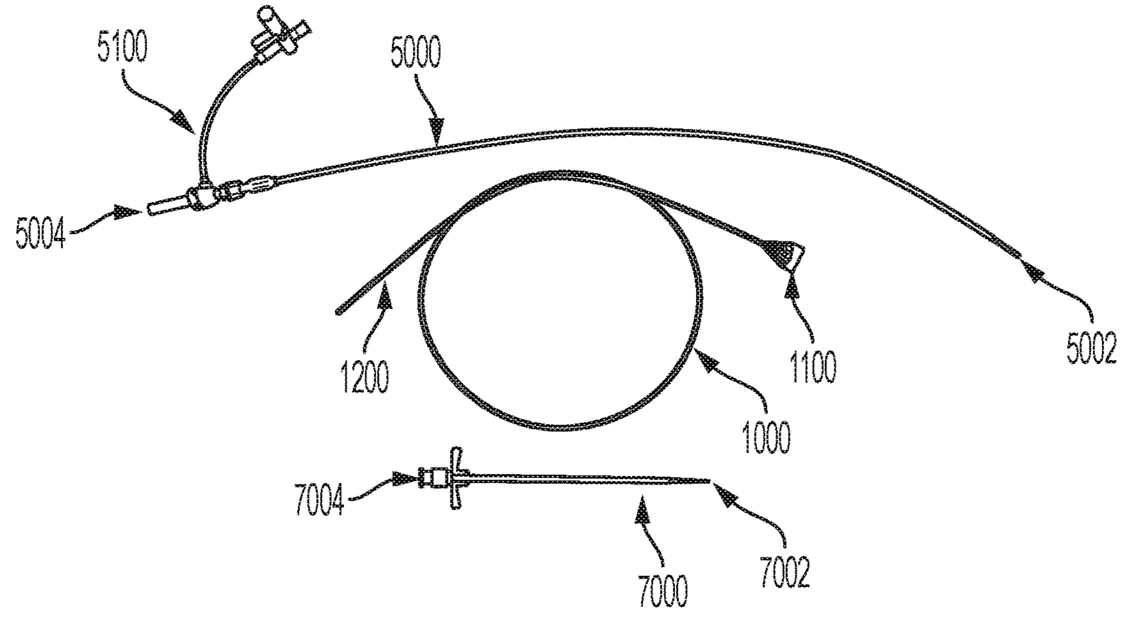
FIGS. 7A to 7L are illustrations of a method of assembling an embolic filter system, according to some embodiments.

Turning now to FIG. 6 a flow chart is illustrated that outlines another example method for a medical device assembly including the embolic filter system 1000. As shown, step 6000 includes providing the embolic filter system 1000 as similarly discussed above with regard to step 4000 of FIG. 4. Step 6002 includes providing a delivery catheter as similarly discussed above with regard to step 4002 of FIG. 4. Step 6004 includes providing a constraining sheath, such as a COTS constraining sheath or a constraining sheath specifically designed for use in combination with the embolic filter system 1000. The constraining sheath may optionally be a constraining sheath that is splittable or that is otherwise configured to be torn-away from the embolic filter system 1000 and the delivery system. FIG. 7A provides an illustration of a delivery catheter 5000 with connector 5100, along with the embolic filter system 1000, and a constraining sheath 7000.

Figure 7B:
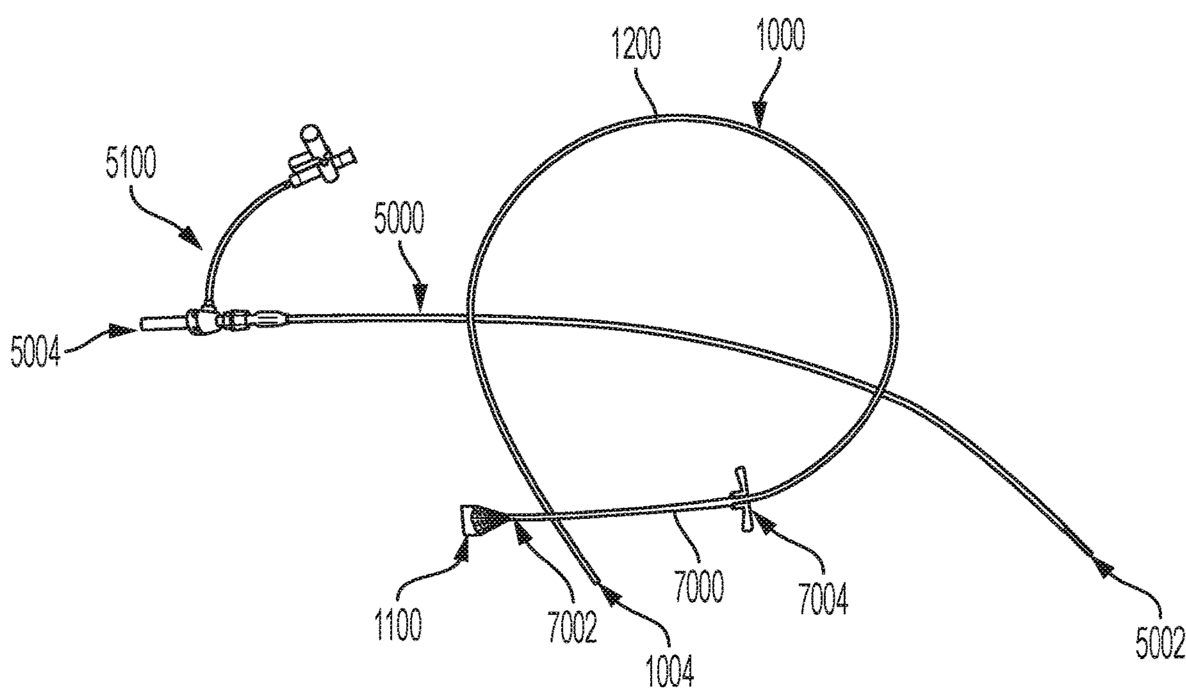
Figure 7C:
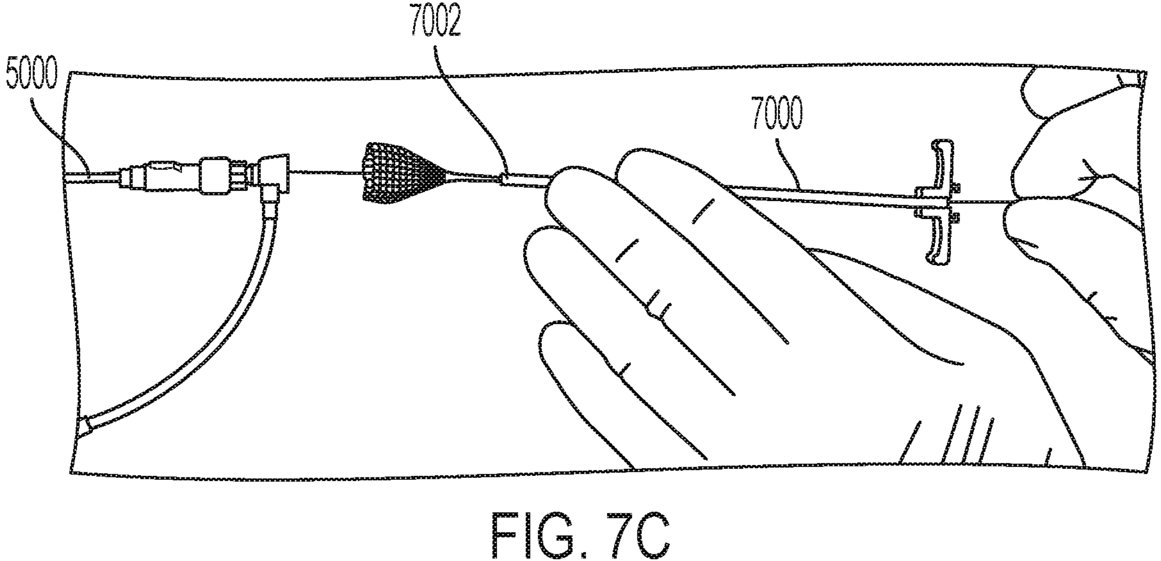

Turning back now to FIG. 6, at step 4006, the proximal end of the embolic filter system 1000 is inserted into the lumen of the constraining sheath and proximally advanced through the lumen of the constraining sheath 7000 until the proximal end of the embolic filter system 1000 extends proximal to the proximal end of the constraining sheath. For example, as shown in FIG. 7B, the proximal end 1004 of the embolic filter system 1000 has been inserted into the lumen of the constraining sheath 7000 at the distal end 7002 of the constraining sheath 7000 and proximally advanced through the lumen of the constraining sheath 7000 until the proximal end 1004 of the embolic filter system 1000 extends proximal to the proximal end 7004 of the constraining sheath 7000.

Turning back now to FIG. 6, at step 6008, the embolic filter system 1000 is proximally withdrawn until the filter 1100 is received within the lumen of the constraining sheath 7000. FIGS. 7C to 7F illustrate the proximal withdrawal of the embolic filter system 1000 relative to the constraining sheath 7000, where the embolic filter system 1000 is withdrawn such that the filter 1100 is partially received within the lumen of the constraining sheath 7000 in FIGS. 7C to 7E, and where the embolic filter system 1000 is withdrawn such that the filter 1100 is completely received within the lumen of the constraining sheath in FIG. 7F. In various examples, as described further below, the withdrawal of the embolic filter system 1000 relative to the constraining sheath 7000 may optionally be performed with the delivery catheter 5000 inserted within the vasculature. In some examples, the withdrawal of the embolic filter system 1000 relative to the constraining sheath 7000 may also optionally be performed with a guidewire extending through one or more of the delivery catheter 5000, the embolic filter system 1000, and the constraining sheath 7000, as shown in FIGS. 7C to 7F.

Figure 7D:
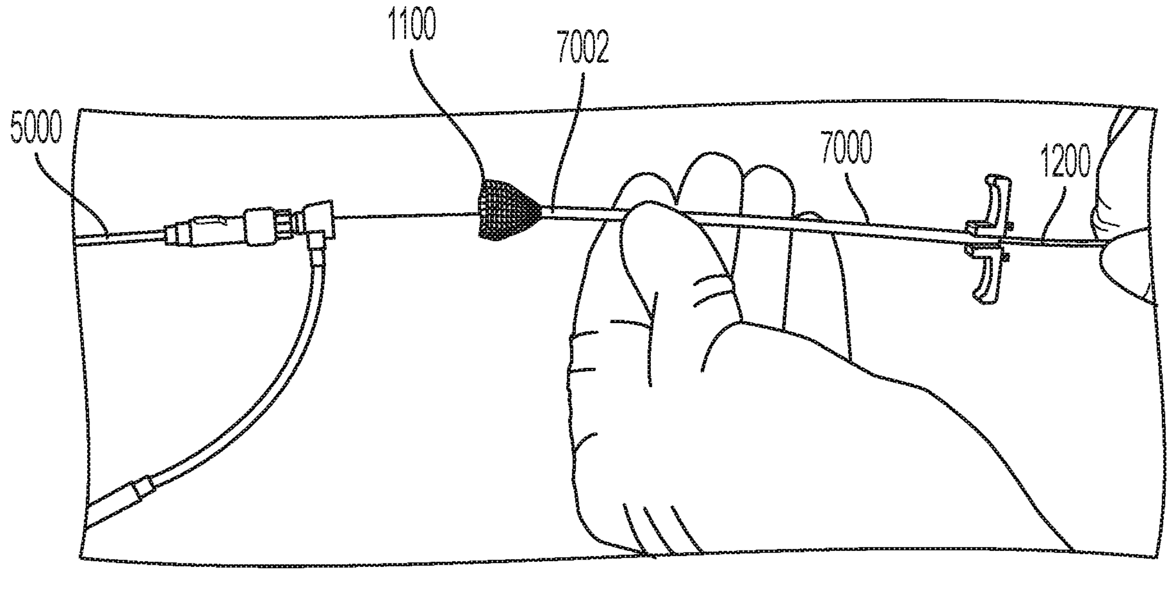
Figure 7E:
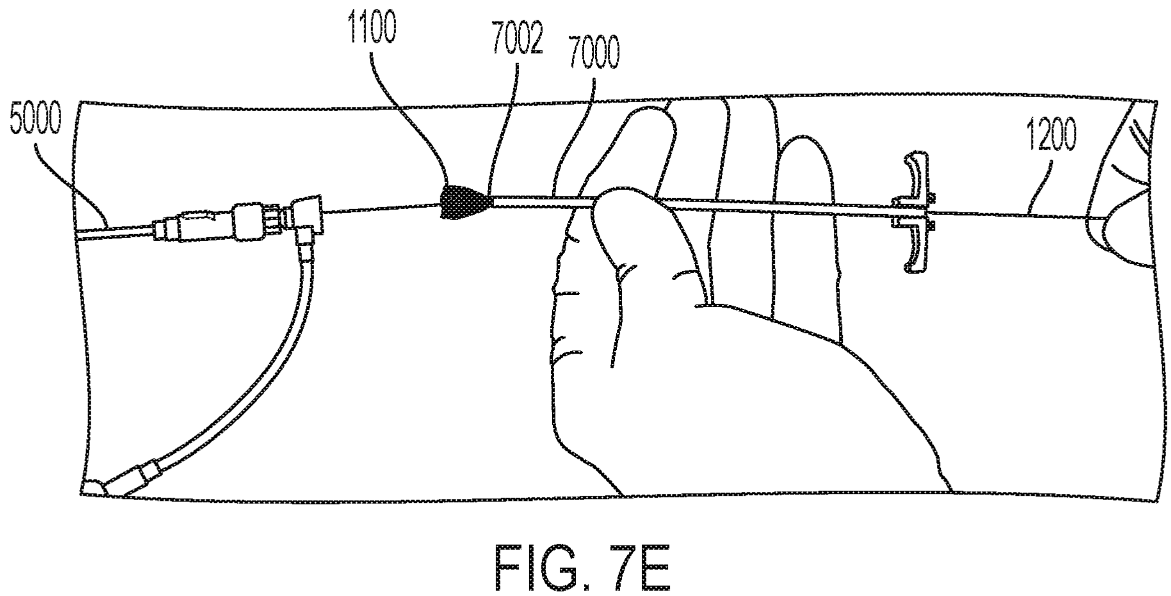
Figure 7F:
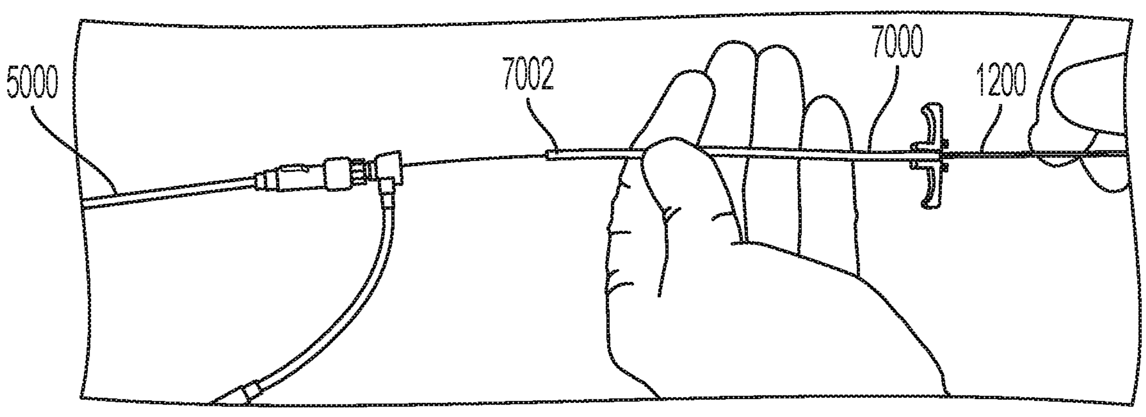

Additionally, in some examples, the elongate element 1200 may have one or more visible markers on the proximal end (e.g. the end of the elongate element 1200 that is being handled by the operator in FIG. 7D) and one or more visible markers on the distal end (e.g. proximate the filter 1100) such that the operator can see how far the filter 1100 coupled to the distal end of the elongate element 1200 is currently disposed within the patient's body by observing the position of each of the markers. In some examples, the proximal markers are visible to the unaided eye while the distal markers are visible under fluoroscopy (e.g., radiopaque). In some examples, one or both of the proximal and distal ends includes only one visible marker. In some example, the visible markers are located along a portion of the length of the elongate element 1200 in the regular or varying increments (e.g., increments of 1 mm, 0.5 cm, 1 cm, 2 cm, or any other suitable increments as deemed useful for the operator). Similarly, visible markers may also be located on the opposite end of the elongate element 1200 or along a length of the filter 1100 and/or the articulation section 1118. As mentioned, in some examples, the visible markers located on the distal end are radiopaque markers made from materials such as high-visibility tantalum or other metals or alloys that are visible in fluoroscopic images. By using the markers located on either or both the proximal and distal ends, the operator can better understand the relative position of the filter 1100 in the body of a patient.

Figure 7G:
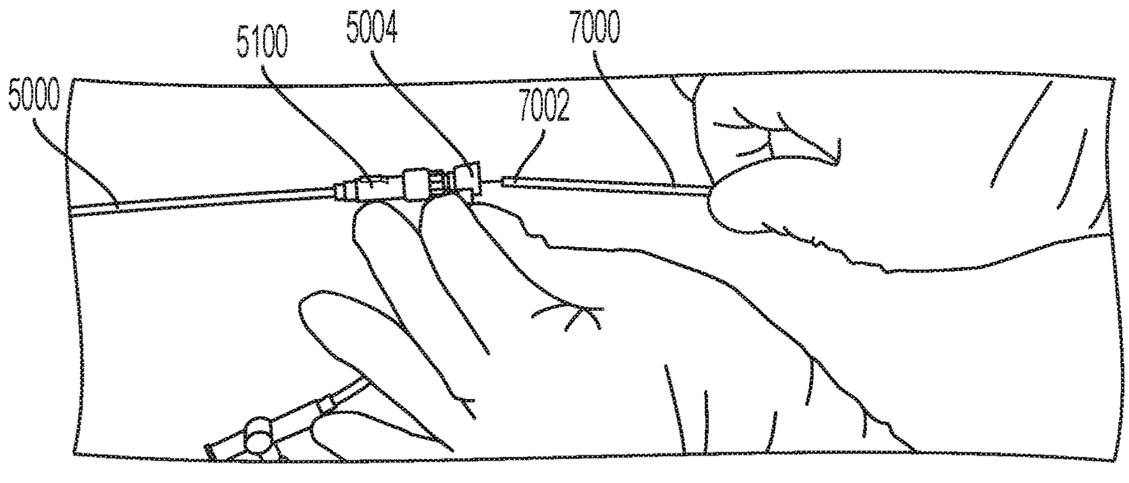
Figure 7H:
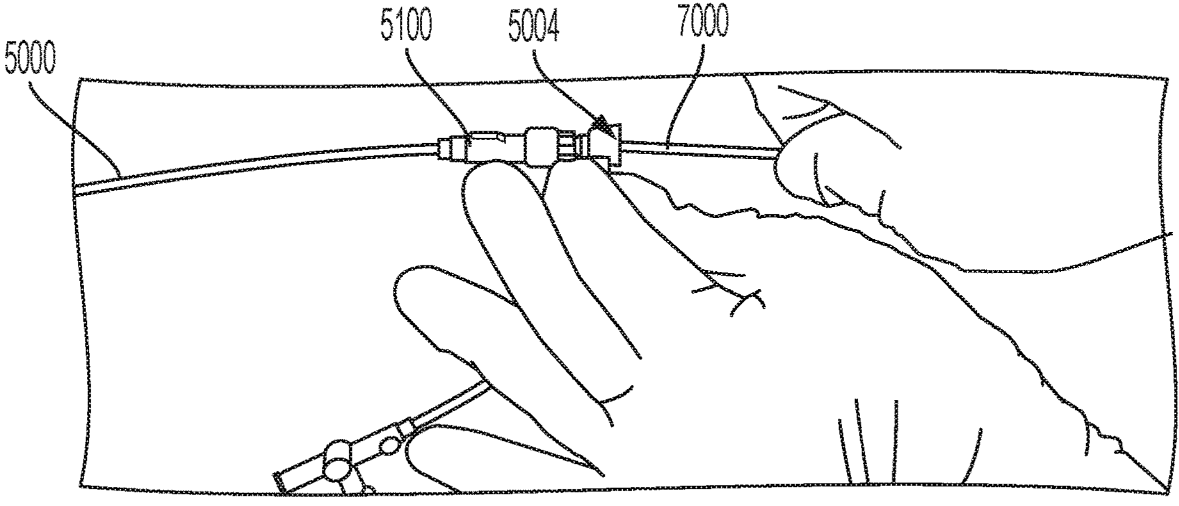

Turning back now to FIG. 6, at step 6010, the distal end of the constraining sheath is inserted into the lumen of the delivery catheter at the proximal end of the delivery catheter. For example, turning now to FIGS. 7G and 7H, with the filter 1100 of the embolic filter system 1000 constrained within the lumen of the constraining sheath 7000, the distal end 7002 of the constraining sheath 7000 is inserted into the lumen of the delivery catheter 5000 at the proximal end 5004 of the delivery catheter 5000. In some example, this may include inserting the distal end 7002 of the constraining sheath 7000 into a connector of the delivery catheter 5000, such as connector 5100. FIG. 7G shows the constraining sheath 7000 with the filter 1100 of the embolic filter system 1000 constrained therein being advanced toward the proximal end 5004 of the delivery catheter 5000, and FIG. 7H shows the distal end 7002 of the constraining sheath 7000 inserted within the lumen of the delivery catheter 5000 at the proximal end 5004 of the delivery catheter 5000.

Figure 7I:
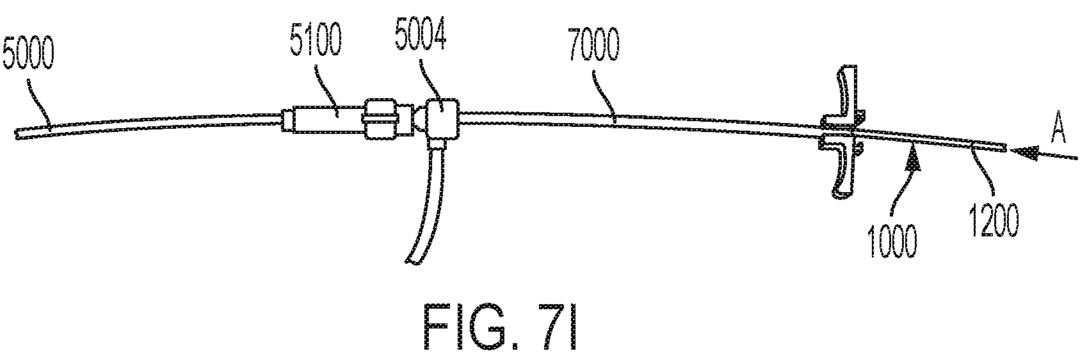
Figure 7J:
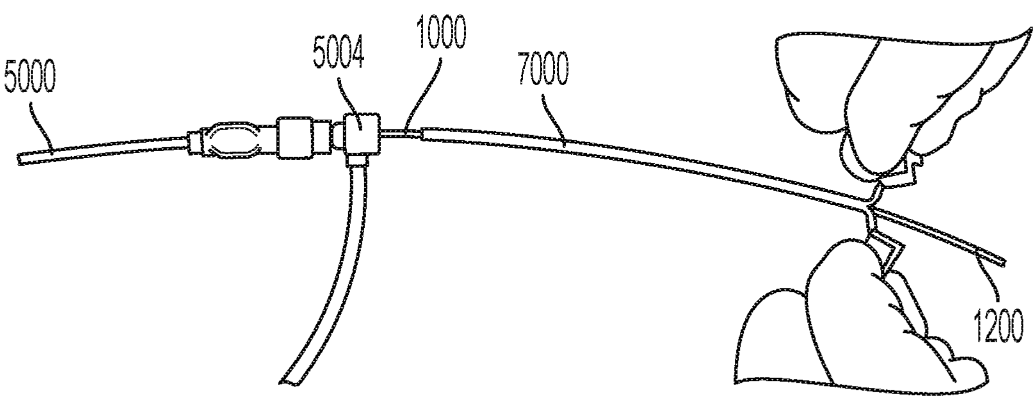

Turning back now to FIG. 6, at step 6012, with the distal end of the constraining sheath inserted in the lumen of the delivery catheter at the proximal end of the delivery catheter, the embolic filter system 1000 is distally advanced relative to the constraining sheath and the delivery catheter until the filter 1100 is received within the lumen of the delivery catheter. For example, as shown in FIG. 7I, with the distal end 7002 of the constraining sheath 7000 inserted in the lumen of the delivery catheter 5000 at the proximal end 5004 of the delivery catheter, the embolic filter system 1000 is distally advanced in the direction of arrow "A" relative to the constraining sheath 7000 and the delivery catheter 5000 until the filter 1100 is received within the lumen of the delivery catheter 5000. FIG. 7J shows, in part, the embolic filter system 1000 inserted into the lumen of the delivery catheter 5000 such that the filter 1100 is received within and constrained by the delivery catheter 5000 in a delivery configuration (e.g., radially constrained).

Turning back now to FIG. 6, after the filter 1100 of the embolic filter system 1000 is received within the lumen of the delivery catheter, the constraining sheath is removed in accordance with step 6014. In various examples, the constraining sheath 7000 is removed from the lumen of the delivery catheter 5000 during removal. In some examples, the constraining sheath 7000 proximally advanced along and relative to the elongate element 1200 of the embolic filter system 1000 until the distal end 7002 of the constraining sheath clears or translates to a position distal to the proximal end 1004 of the embolic filter system 1000. However, in some examples, as mentioned above, the constraining sheath 7000 is splittable or is otherwise configured to be torn away from the embolic filter system 1000 and the delivery catheter 5000. Such splittable constraining sheaths may provide ease of removal where one or more connectors (e.g., Tuohy-Borst connector) are coupled to the elongate element 1200 of the embolic filter system 1000 proximal to the constraining sheath 7000. In some such examples, the splittable constraining sheath can be removed from the embolic filter system 1000 and the delivery catheter 5000 without requiring removal of the connector coupled to the elongate element 1200 of the embolic filter system 1000 proximal to the constraining sheath 7000.

Figures 7K, 7L:
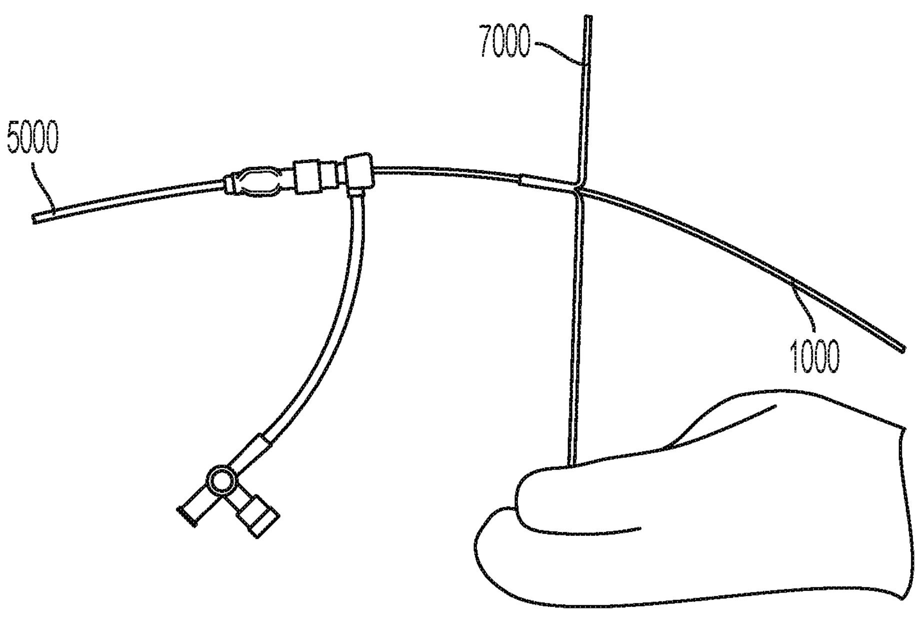

An example removal of such a splittable constraining sheath 7000 is shown in FIGS. 7J and 7K, where the constraining sheath 7000 is shown being split in to two sections for removal from the embolic filter system 1000 and the delivery catheter 5000. FIG. 7L shows the embolic filter system 1000 with the filter 1100 completely received within the lumen of the delivery catheter 5000.

With the filter 1100 completely received within the lumen of the delivery catheter 5000, as shown in FIG. 7L, the delivery catheter 5000 can be inserted into the vasculature of a patient and advanced to a treatment site therein, whereinafter the embolic filter system 1000 can be advanced relative to the delivery catheter 5000 (e.g., by one or more of distally advancing the embolic filter system 1000 relative to the delivery catheter 5000 and proximally withdrawing the delivery catheter 5000 relative to the embolic filter system 1000) such that the filter 1100 extends distally from the distal end 5002 of the delivery catheter 5000. As mentioned above, one or more portions of the filter 1100, such as the structural element 1108, are configured to radially expand to interrupt blood flow to filter embolic debris therefrom.

Figure 8:
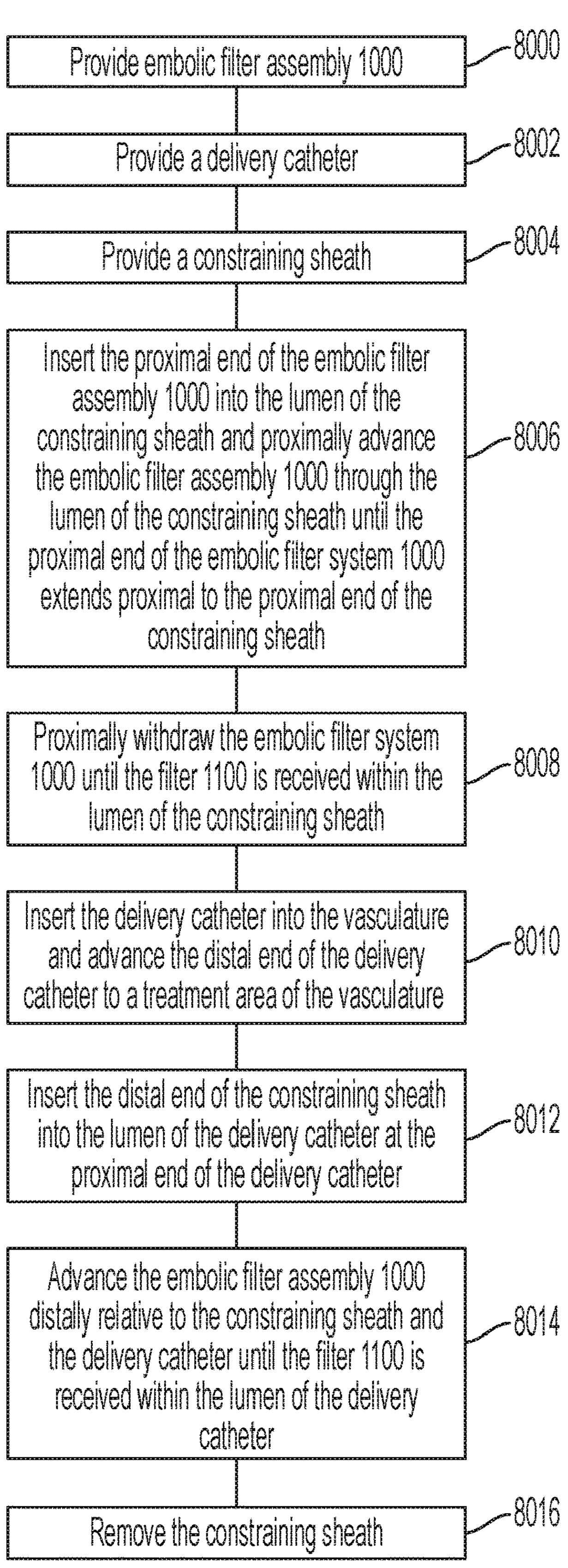
FIG. 8 is a flow chart of a method of implanting an embolic filter system, according to some embodiments.

Turning now to FIG. 8 a flow chart is illustrated that outlines an example method for delivering a medical device including the embolic filter system 1000 to a region within a patient's vasculature. As shown, steps 8000 to 8008 are consistent with steps 6000 to 6008 described above with respect to FIG. 6. At step 8010, the delivery catheter is inserted into the vasculature of a patient and advanced until a distal end of the delivery catheter is positioned at a treatment area of the vasculature. Accordingly, it is to be appreciated that while the discussion above includes advancing the delivery catheter to a treatment area within a patient's vasculature after the embolic filter system 1000 is received within the delivery catheter 5000, in some examples, the delivery catheter 5000 may alternatively be inserted into the vasculature of the patient and advanced until a distal end of the delivery catheter is positioned at a treatment area of the vasculature prior to inserting the embolic filter system 1000 into the delivery catheter 5000.

At step 8012, the distal end of the constraining sheath is inserted into the lumen of the delivery catheter at the proximal end of the delivery catheter. This step is largely consistent with step 6010 of FIG. 6, with the exception that step 8012 is being performed with the delivery catheter in situ (i.e., while the delivery catheter is inserted within the patient's vasculature. Accordingly, reference is drawn to FIGS. 7G and 7H, which illustrate the distal end 7002 of the constraining sheath 7000 being inserted into the lumen of the delivery catheter 5000 at the proximal end 5004 of the delivery catheter 5000. Those of skill should thus appreciate that the inventive concepts of the present disclosure provide for the ability to perform the step of inserting the constraining sheath into the lumen of the delivery catheter at the proximal end of the delivery catheter in situ or alternatively prior to advancement of the delivery catheter to the treatment area within the vasculature.

Such a versatile system provides that the embolic filter system 1000 can be delivered to remote regions of the vasculature that might not be accessible with conventional systems. Such a system also provides that the embolic filter system 1000 can be delivered to remote regions of the vasculature while minimizing trauma to the vasculature. For instance, those of skill will appreciate that the stiffness of a delivery catheter increases as additional components are received within its lumen. Relatively stiff delivery catheters may not be operable to navigate tortuous anatomy to reach certain regions of the vasculature and/or may traumatize the vasculature as a result of inflexibility. The embolic filter system 1000 described herein provides that a relatively flexible delivery catheter can be first advanced to a treatment area within the vasculature (e.g., such as within or through a relatively tortuous region), without one or more additional components disposed therein that would otherwise operate to increase the stiffness of the delivery catheter. Moreover, such a configuration provides that the delivery catheter can operate as a protective boundary and bearing surface separating the embolic filter system 1000 from the surrounding vasculature as the embolic filter system 1000 is advanced to the treatment area.

Steps 8014 and 8016 are consistent with steps 6012 and 6014 described above with respect to FIG. 6. Similarly, as illustrated and described above, it is to be appreciated that after the filter 1100 of the embolic filter system 1000 is advanced through the lumen of the delivery catheter to the treatment site, the embolic filter system 1000 is operable to be deployed from the distal end of the delivery catheter (e.g., by one or more of distally advancing the embolic filter system 1000 relative to the delivery catheter and proximally withdrawing the delivery catheter relative to the embolic filter system 1000) such that the filter 1100 extends distally from the distal end of the delivery catheter and expands to interrupt blood flow to filter embolic debris therefrom.

The versatility of the embolic filter system 1000 illustrated and descried herein also provides for ease of removal of the embolic filter system 1000 from the vasculature and repositioning of the same in-situ. For example, during or subsequent to a deployment of the embolic filter system 1000 within the vasculature, and operator can manipulate the angular relationship between the filter 1100 and the elongate element 1200 of the embolic filter system 1000 to achieve a better alignment of the filter 1100 with the vessel within which it is deployed. For instance, as mentioned above, the embolic filter system 1000 is operable to have a relative articulation occur between the filter 1100 and the elongate element 1200 by way of an articulation section 1118 bending or curving in response to advancement and retraction of the elongate element 1200. When the filter 1100 is deployed within a vessel, one or more portions of the filter engage the vessel wall, thereby creating an engagement between the filter 1100 and the vessel.

With the filter 1100 engaged with the vessel, the elongate element 1200 is operable to be advanced or retracted. Under certain conditions, advancement of the elongate element 1200 with the filter 1100 engaged, at least in part, with the vessel wall causes the embolic filter system 1000 to undergo a compressive loading condition. In certain instances, such as those where the filter 1100 is improperly aligned with the vessel in which it is deployed, such a compressive loading condition causes the articulation section 1118 of the embolic filter system 1000 to bend, thereby causing a relative articulation between the filter 1100 (or at least a distal end thereof) and the elongate element 1200, as discussed above. Conversely, under certain conditions, retraction of the elongate element 1200 with the filter 1100 engaged, at least in part, with the vessel wall causes the embolic filter system 1000 to undergo a tensile loading condition. In certain instances, such as those where the filter 1100 misaligned with the elongate element 1200, such a tensile loading condition causes the articulation section 1118 of the embolic filter system 1000 to straighten, thereby causing a relative articulation between the filter 1100 (or at least a distal end thereof) and the elongate element 1200 such that the filter 1100 and the elongate element 1200 migrate toward alignment with one another. Thus, the elongate element 1200 can be advanced and retracted to cause articulation between the filter 1100 (or at least a distal end thereof) and the elongate element 1200, that can be utilized to achieve a proper alignment of the filter 1100 within the vessel. It should be appreciated that proper alignment of the filter 1100 within the vessel does not require alignment between the filter 1100 and the elongate element 1200, and may require misalignment between the filter 1100 and the elongate element 1200.

While the embolic filter system 1000 of the various examples and illustrations described above includes a filter 1100 having an articulation section 1118 incorporated therein, in some alternative examples, the embolic filter system 1000 may additionally or alternatively include one or more independent articulation elements that are positioned proximal to the filter 1100 and that provide for articulation between the filter 1100 and one or more portions of the elongate element 1200. That is, in some example, the embolic filter system 1000 includes an articulation element that is independent of (e.g., not part of) the filter 1100. For instance, the filter 1100 may include the structural element 1108 without also including the articulation section 1118.

The articulation element in such examples may be consistent in form in function with the articulation section 1118 of the filter 1100 described above, with the exception that the articulation element is not an integral portion of the filter 1100 but is instead an independent component that is coupled (either directly or indirectly) to one or more of the filter 1100 and the elongate element 1200. Thus, in some examples, the articulation element includes a tubular construct that has been helically cut or slotted. As mentioned above, in those examples including a cut tube, the cuts in the tube to form the coil/helix or slotted segment extend through the thickness of the tube (e.g., from an exterior surface of the tube to the interior surface of the tube) such that the interior lumen of the tube is exposed. Such full thickness cuts in the tube provide gaps that can accommodate bending in one or more related portions of the tube (e.g., bending of one or more helical windings).

Figure 9:
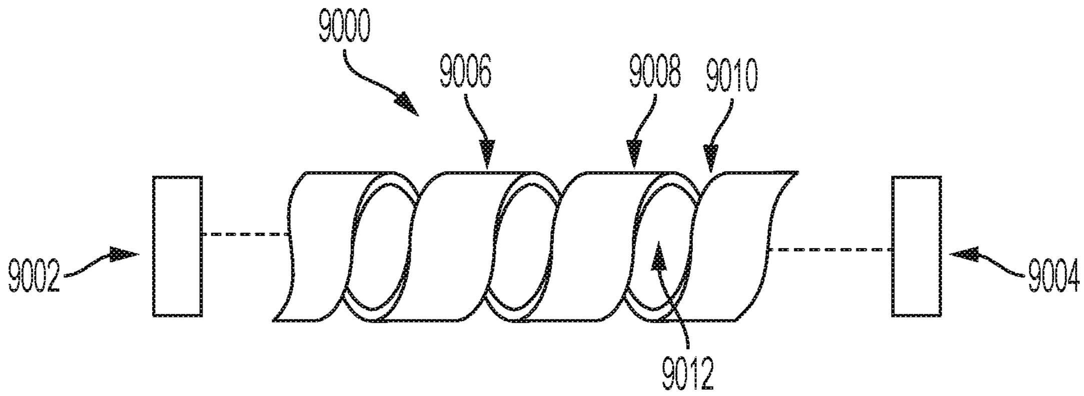
FIG. 9 is an illustration of an articulation element for use in an embolic filter system, according to some embodiments.

FIG. 9 shows an example articulation element 9000. As shown, the articulation element has a first end 9002 and a second end 9004. The first and second ends 9002 and 9004 may be configured to interface with one or more of the filter 1100 and the elongate element 1200. For instance, in some examples, the articulation element 9000 may be incorporated into the embolic filter system 1000 by coupling the first end 9002 of the articulation element 9000 to the proximal end 1104 of the filter 1100, and by coupling the second end 9004 of the articulation element 9000 to the distal end 1204 of (or a distal portion of) the elongate element 1200. In such examples, the articulation element 9000 is positioned between the filter 1100 and the elongate element 1200 such that the filter 1100 and the elongate element 1200 are free to articulate relative to one another.

Additionally, as shown, the articulation element 9000 includes a plurality of helical windings, such as helical windings 9006 and 9008. In some examples, as mentioned above, the helical windings are formed in conjunction with cutting through a thickness of a tube in a helical pattern to create one or more helical windings. In various examples, adjacent helical windings are separated from one another by a helical gap 9010. As shown, the helical gap 9010 exposes the lumen 9012 of the articulation element 9000.

In various examples, and consistent with the discussion above, an embolic filter system, such as embolic filter system 1000, having the articulation element 9000 in addition to, or in lieu of the articulation section 1118 may be configured such that the membrane 1300 extends along one or more of the exterior of the articulation element 9000 and the interior luminal wall of the articulation element 9000. As such, the membrane 1300 is operable to filter embolic debris, from blood escaping through the gap 9010. That is, the membrane 1300 is operable to prevent embolic debris from escaping the embolic filter system through gap 9010 in the articulation element 9000. In some examples, the membrane 1300 may be blood impermeable in the region of the articulation element 9000.

In some embodiments, the elongate element 1200 is configured such that its length can be easily modified in association with and endovascular procedure. For instance, in some examples, the elongate element 1200 is operable to be cut such that a length of the elongate element can be modified from a first length, to a second shorter length. In some examples, the elongate element 1200 is configured such that the length of elongate element 1200 can be modified while the embolic filter system 1000 is received within the lumen of the delivery catheter 5000. In some examples, an attachable/detachable hub is coupled to the proximal end of the elongate element 1200 to fluidly seal the lumen of the delivery catheter 5000. For example, the hub may have a Luer taper connection, a hose barb connection, or a combination thereof (e.g., Luer-to-barb fitting connection) as used to form a leak-free connection at the proximal end of the elongate element 1200, as suitable. In some examples, the hub may be permanently attached or coupled to the proximal end of the elongate element 1200 and in others the hub may be removably attached thereto.

In some examples, the elongate element 1200 includes a plurality of predetermined sections that are configured to be removed. For instance, in some examples, the elongate element 1200 includes a first removable section and a second removable section, such that either one or both of the first and second removable sections can be removed to modify the length of the elongate element from the first length to the second shorter length. In some examples, the removable sections may be configured to be removed by way of cutting. In some other examples, the removable sections may be configured to be additionally or alternatively removed by way of twisting, bending, or pulling the removable section relative to the remainder of the elongate element 1200.

In some examples, one or more portions or components of the embolic filter system 1000, such as the elongate element 1200, may be color-coded to indicate a diameter of the elongate element 1200, wherein a first color indicates a first diameter (e.g., 6 Fr) and wherein a second color indicates a second different diameter. Such color-coding can help users identify a proper diameter for used with a COTS delivery catheter in association with an endovascular procedure.

It should be appreciated that the configurations discussed herein are scalable in that they can be scaled up or scaled down for different applications. That is, while certain of the configurations discussed herein are illustrated and described in association with placement within the aortic arch, for example, the versatility of the system provides for implementation in virtually any other area of the patient's vasculature. For example, the various configurations discussed herein may be scaled for application within various peripheral vessels and lumens such as the brachiocephalic artery, and/or the carotid artery, and/or the subclavian artery. Likewise, as it relates to the aortic arch, the present disclosure can be used in connection with femoral, transapical and thoracotomy approaches. Moreover, this disclosure should not be interpreted as limiting application to the vessels proximate the heart. For instance, the devices and systems described herein may be implemented throughout the vasculature of the body including vasculature above and below the heart to prevent the migration of embolic debris during various other revascularization procedures. Additionally, the embodiments can be used in connection with not just humans, but also various organisms having mammalian anatomies. Thus, it is intended that the embodiments described herein cover the modifications and variations within the scope of this disclosure. As such, the embolic filter system 1000 may be formed in a variety of different sizes, which may optionally be based on COTS delivery catheter sizes such that the embolic filter system 1000 can be produced in a variety of sizes that can be used in association with the variety of sized of COTS delivery catheters. As mentioned above, one or more components of the embolic filter system 1000 may be color coded based on such sizing.

The inventive scope of this application has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the inventive scope.

What is claimed:

1. A medical device comprising:

an elongate element having a first end and a second end; and an embolic filter assembly comprising a frame having an attachment section, a capture section distal to the attachment section, and an intermediate section between the attachment section and the capture section, wherein the intermediate section forms a segment that is adapted to allow for relative articulation between the capture section of the frame and the attachment section of the frame, and the attachment section has a body defining a first longitudinal axis and a lumen extending through the body for receiving the elongate element, the attachment section of the frame defines a plurality of apertures spaced along the first longitudinal axis and providing access to one of the first and second ends of the elongate element that is coupled to the attachment section, and the attachment section is configured to couple the elongate element to the attachment section using an attaching material received through one or more of the apertures, such that the attachment section is attached to the elongate element in such a manner as to preserve relative articulation between the capture section of the frame and the attachment section of the frame.

2. The medical device of claim 1, wherein the capture section is radially expandable relative to the attachment section such that the embolic filter assembly is configured to transition between a compressed state and an expanded state in situ.

3. The medical device of claim 1, wherein the capture section is radially expandable relative to the intermediate section.

4. The medical device of claim 1, wherein the frame is configured such that the capture section is self-expandable.

5. The medical device of claim 1, wherein the frame includes a metallic alloy.

6. The medical device of claim 5, wherein the metallic alloy includes nitinol.

7. The medical device of claim 1, wherein the frame is a unibody such that the attachment section, the capture section, and the intermediate section define a single monolithic component.

8. The medical device of claim 1, wherein the segment of the intermediate section is helically shaped.

9. The medical device of claim 1, wherein the frame is a laser cut tube.

10. The medical device of claim 9, wherein the intermediate section is defined by a helical cut through the intermediate section that exposes a lumen of the laser cut tube.

11. The medical device of claim 1, wherein the attachment section, the capture section, and the intermediate section are affixed to one another.

12. The medical device of claim 11, wherein one or more of the capture section and the intermediate section comprise a wire frame.

13. The medical device of claim 12, wherein the intermediate section includes a helically wound wire.

14. The medical device of claim 1, wherein the segment of the intermediate section has a slotted pattern that is adapted to bend.

15. The medical device of claim 1, wherein the capture section defines a second longitudinal axis, and wherein the intermediate section is adapted to bend such that the first longitudinal axis can be deflected up to 270 degrees relative to the second longitudinal axis.

16. The medical device of claim 1, wherein the capture section defines a second longitudinal axis, and wherein the intermediate section is adapted to bend such that the first longitudinal axis can be deflected up to 180 degrees relative to the second longitudinal axis.

17. The medical device of claim 1, wherein the capture section defines a second longitudinal axis, and wherein the intermediate section is adapted to bend such that the first longitudinal axis can be deflected up to 90 degrees relative to the second longitudinal axis.

18. The medical device of claim 1, wherein the frame has a first end and a second end and a lumen extending through the frame from the first end of the frame to the second end of the frame.

19. The medical device of claim 1, wherein the embolic filter assembly further comprises a filter material disposed along the frame.

20. The medical device of claim 19, wherein the filter material is disposed along the intermediate section of the frame.

21. The medical device of claim 19, wherein the filter material is impermeable to embolic debris greater than about one hundred micrometers (100 μm).

22. The medical device of claim 19, wherein the filter material is configured to constrain elongation of the intermediate section to less than a yield point of the intermediate section.

23. The medical device of claim 19, wherein the filter material is configured to stretch to accommodate one or more of bending and elongation of the intermediate section of the frame, wherein a yield strength of the filter material exceeds a yield strength of the intermediate section.

24. The medical device of claim 19, wherein the filter material includes a polymeric material.

25. The medical device of claim 24, wherein the polymeric material includes ePTFE.

26. The medical device of claim 1, wherein one or more of the capture section, the attachment section, and the elongate element are operable to articulate about the intermediate section.

27. The medical device of claim 1, wherein the segment includes a helically cut portion that includes at least: a first helical portion with a first pitch providing a first degree of articulation, and a second helical portion with a second pitch providing a second degree of articulation that is greater than the first degree of articulation.

28. The medical device of claim 1, wherein the attachment section further comprises one or more projections extending circumferentially along an interior or exterior of the attachment section.

29. The medical device of claim 1, wherein the attachment section further comprises one or more projections extending longitudinally along an interior or exterior of the attachment section.

30. The medical device of claim 1, wherein the embolic filter assembly comprises a first filter material disposed along an exterior of the frame and a second filter material disposed at least partially along an interior of the frame.

31. The medical device of claim 1, wherein the attaching material comprises an adhesive material or a thermal bonding material.

32. The medical device of claim 1, further comprising:

a filter material with a first portion of the filter material disposed about an exterior of the capture section and a second portion of the filter material disposed about an exterior of the intermediate section.

33. The medical device of claim 32, wherein the capture section is configured to capture embolic debris, and the filter material operates to filter and retain the captured embolic debris within the embolic filter assembly.

34. The medical device of claim 33, wherein the second portion of the filter material operates to increase a tensile strength of the intermediate section.

35. A medical device comprising:

an elongate element having a first end and a second end; and an embolic filter assembly comprising a unibody frame having an attachment section, a capture section distal to the attachment section, and an intermediate section between the attachment section and the capture section, wherein the intermediate section forms a helical winding that is adapted to allow for relative articulation between the capture section of the unibody frame and the attachment section of the unibody frame, and the attachment section has a body and a lumen extending through the body for receiving the elongate element, the attachment section of the unibody frame defines a plurality of rows of apertures providing access to one of the first and second ends of the elongate element that is coupled to the attachment section, and the attachment section is configured to couple the elongate element to the attachment section using an attaching material received through one or more of the apertures, such that the attachment section is attached to the elongate element in such a manner as to preserve relative articulation between the capture section of the unibody frame and the attachment section of the unibody frame.

36. The medical device of claim 35, further comprising:

a filter material with a first portion of the filter material disposed about an exterior of the capture section and a second portion of the filter material disposed about an exterior of the intermediate section.

37. The medical device of claim 36, wherein the capture section is configured to capture embolic debris, and the filter material operates to filter and retain the captured embolic debris within the embolic filter assembly.

38. The medical device of claim 37, wherein the second portion of the filter material operates to increase a tensile strength of the intermediate section.

39. A medical device comprising:

an elongate element having a first end and a second end; and an embolic filter assembly comprising a frame having an attachment section, a capture section distal to the attachment section, and an intermediate section between the attachment section and the capture section, wherein the intermediate section forms a segment that is adapted to allow for relative articulation between the capture section of the frame and the attachment section of the frame, and the attachment section has a body and a lumen extending through the body for receiving the elongate element, the attachment section of the frame defines a plurality of circular apertures providing access to one of the first and second ends of the elongate element that is coupled to the attachment section, and the attachment section is configured to couple the elongate element to the attachment section using an attaching material received through one or more of the apertures, such that the attachment section is attached to the elongate element in such a manner as to preserve relative articulation between the capture section of the frame and the attachment section of the frame.

40. The medical device of claim 39, further comprising:

a filter material with a first portion of the filter material disposed about an exterior of the capture section and a second portion of the filter material disposed about an exterior of the intermediate section.

41. The medical device of claim 40, wherein the capture section is configured to capture embolic debris, and the filter material operates to filter and retain the captured embolic debris within the embolic filter assembly.

42. The medical device of claim 41, wherein the second portion of the filter material operates to increase a tensile strength of the intermediate section.

* * * * *